(12) United States Patent
Gross et al.

(10) Patent No.: US 7,972,822 B2
(45) Date of Patent: Jul. 5, 2011

(54) ENZYME-CATALYZED POLYCARBONATE AND POLYCARBONATE ESTER SYNTHESIS

(75) Inventors: Richard A. Gross, Plainview, NY (US); Zhaozong Jiang, New Haven, CT (US)

(73) Assignee: Polytechnic Institute of New York University, Brooklyn, NY (US)

(*) Notice: Subject to any disclaimer, the term of this patent is extended or adjusted under 35 U.S.C. 154(b) by 223 days.

(21) Appl. No.: 12/193,391

(22) Filed: Aug. 18, 2008

(65) Prior Publication Data
US 2009/0047717 A1  Feb. 19, 2009

Related U.S. Application Data

(63) Continuation-in-part of application No. 12/192,628, filed on Aug. 15, 2008.

(60) Provisional application No. 60/956,500, filed on Aug. 17, 2007.

(51) Int. Cl.
*C08G 63/00* (2006.01)
*C08G 64/00* (2006.01)

(52) U.S. Cl. ........ 435/135; 435/136; 510/309; 510/320; 528/271; 528/272; 546/89; 546/150

(58) Field of Classification Search ............... 435/135, 435/136; 510/309, 320; 528/271, 272; 546/89, 546/150
See application file for complete search history.

(56) References Cited

U.S. PATENT DOCUMENTS

| | | | |
|---|---|---|---|
| 2009/0162337 A1* | 6/2009 | Gross et al. | 424/94.6 |
| 2009/0298139 A1* | 12/2009 | Zou et al. | 435/118 |
| 2010/0041856 A1* | 2/2010 | Gross et al. | 528/274 |

* cited by examiner

*Primary Examiner* — Terressa M Boykin
(74) *Attorney, Agent, or Firm* — Laurence P. Colton; Smith Risley Tempel Santos LLC

(57) ABSTRACT

An enzymatic process for preparing aliphatic polycarbonates via terpolymerization or transesterification using a dialkyl carbonate, an aliphatic diester, and an aliphatic diol or triol reactant. A catalyst having an enzyme capable of catalyzing an ester hydrolysis reaction in an aqueous environment is subsequently added to the reaction mixture. Next, polymerization of the reaction proceeds for an allotted time at a temperature $\leq 100°$ C. Finally, the copolymer is isolated from an the catalyst via filtration.

20 Claims, 10 Drawing Sheets

US 7,972,822 B2

ENZYME-CATALYZED POLYCARBONATE AND POLYCARBONATE ESTER SYNTHESIS

STATEMENT OF RELATED APPLICATIONS

This application is a continuation-in-part of and claims the benefit of U.S. patent application Ser. No. 12/192,628 having a filing date of 15 Aug. 2008, which is based on and claims the benefit of U.S. Provisional Patent Application No. 60/956,500 having a filing date of 17 Aug. 2007.

BACKGROUND OF THE INVENTION

1. Technical Field

This invention relates to an enzymatic process for preparing aliphatic polycarbonates and a method of preparation of prepolymers, using cyclic lactones as one reactant.

2. Related Art

Polycarbonates are a particular group of useful polymers. Many polycarbonates can be molded and thermoformed into established products used in large quantities by various market sectors. In many cases, polycarbonate synthesis is accomplished using organometallic catalysts. For example, poly(ether-carbonate) polyols can be synthesized via copolymerization of propylene oxide with carbon dioxide using glycerol-propylene oxide copolymer as an initiator and zinc hexacyanocolbaltate as catalyst. Similar poly(ether-carbonate) polyols can be prepared via polycondensation of diethyl carbonate with aliphatic diol and glycerol-ethylene oxide copolymer using $Ti(OBu)_4$ as a catalyst. Also, aliphatic polycarbonate polyols reportedly can be prepared using condensation copolymerization of ethylene carbonate with trimethylolpropane and aliphatic diols.

Further, various chemical synthetic methods have been employed to prepare aliphatic poly(carbonate-co-esters). For example, synthesis of poly(butylenecarbonate-co-butylenesuccinate) was disclosed using the following two procedures: (a) polycondensation of dimethyl succinate and diphenyl carbonate with 1,4-butanediol using zinc acetate as catalyst, and (b) chain extension of poly(butylene succinate) diol with diphenyl carbonate using zirconium acetylacetonate as catalyst. In addition, to the above polycondensation methods, reports were found on the preparation of aliphatic poly(carbonate-co-esters) via copolymerization of propylene oxide, carbon dioxide and ε-caprolactone, and ring-opening copolymerization of spiroorthocarbonate and ε-caprolactone.

Enzyme-catalyzed polycondensations between dialkyl carbonate or alkylene divinyl dicarbonate and diol has been known to generate various aliphatic polycarbonates. Also, synthesis of aliphatic polycarbonate polyols using enzyme catalysis has been known. Further, copolymerization of alkylene divinyl dicarbonate with aliphatic triols using Novozym 435 as a catalyst to form hydroxylated aliphatic polycarbonates has also been reported. For the latter, monomer feeds studied include: various activated dicarbonates (e.g., trimethylene divinyl dicarbonate, tetramethylene divinyl dicarbonate, and hexamethylene divinyl dicarbonate) and various triols (e.g., glycerol, 1,2,4-butanetriol, and 1,2,6-trihydroxyhexane). In a typical example, copolymerization reactions of 1,2,4-butanetriol with trimethylene divinyl dicarbonate, tetramethylene divinyl dicarbonate, and hexamethylene divinyl dicarbonate were carried out in bulk at 50° C. for 72 h using 1 wt % immobilized *Candida antarctica* Lipase B (CALB) as a catalyst to form soluble polycarbonates with $M_w$ values of 900, 1 200, and 1 200, respectively. The highest molecular weight ($M_w$=5 500) for hydroxylated polycarbonate was obtained via polycondensation of 1,2,4-butanetriol and hexamethylene divinyl dicarbonate using 10 wt % Novozym 435 catalyst. Furthermore, the use of activated divinyl carbonate monomers results in a commercially impractical approach because of the high cost of these monomers in addition to their poor chemical stability.

Because organometallic catalysts with low activity are employed, high reaction temperatures (up to 220° C.) are required for these prior art processes. This often causes unwanted side reactions (e.g., alcohol dehydration to form olefins) and leads to low product purity. Furthermore, the use of diphenyl carbonate as a comonomer by chemically-catalyzed polycarbonate polymerization reactions results in toxic phenol as a byproduct. Also, the use of organometallic catalysts results in metal contaminants in products that are likely toxic or may limit the applications that products can be used in.

Accordingly, there is a desire for new and more efficient methods to prepare polycarbonates.

SUMMARY OF THE INVENTION

Briefly, this invention describes a practical, scalable method for enzyme-catalyzed copolymerization of dialkyl carbonates (e.g., as diethyl carbonate) and aliphatic diesters with diols. This new methodology for the preparation of poly(carbonate-co-ester) provides an alternative, environmentally benign route to these materials, free of toxic byproducts and metal catalyst residues. The mild reaction conditions and high specificity of enzyme-catalysts allow for the preparation of polycarbonates with excellent control of end-group structure in addition to low polydispersity. High-purity poly(carbonate-co-ester) products may be especially beneficial in medical and electronic applications.

Enzyme catalysis provides a solution to various problems associated with current methodologies of polycarbonate synthesis. For instance, enzyme catalysis reactions run under mild conditions and the catalyst is metal free. Additionally, enzyme-catalysis provide a method for controlling end-group structures at low and high polycarbonate molecular weights, respectively, and providing selectivity and control over branching for polymerizations involving polyols or other multifunctional building blocks. Further, enzyme-catalysis provides the above-mentioned attributes while allowing the synthesis of random or block ester-carbonate copolymers.

The use of enzyme-catalysis for the preparation of functional polycarbonates may include a high tolerance of enzymes to functional groups, and catalyst selectivity that provides control over branching. Enzyme-mediated synthesis of polyester polyols has been successful via copolymerization of aliphatic diacids with polyols (e.g., glycerol, sorbitol) and terpolymerization of diacids with aliphatic diols and polyols.

Immobilized *Candida antarctica* Lipase B (alternatively referred to as CALB, Novozym 435, and N435, from Novozymes) has been successfully employed as a catalyst for terpolymerization of dialkyl carbonate with aliphatic diol and a triol under mild reaction conditions ($\leqq 100°$ C.) to form high purity, metal-free, polycarbonate polyols with $M_w$ up to 100,000. The method disclosed herein represents the first enzyme-catalyzed polycarbonate polyol synthesis from practical, conventional monomer feeds. N435 can be highly regiospecific in catalyzing reactions with triol substrates in which only primary hydroxyl groups react with dialkyl carbonate or alkyl carbonate end groups and participate in chain growth reactions during terpolymerization. Thus, the use of a triol containing only two primary hydroxyls (e.g., glycerol) can result in formation of linear polycarbonate polyols while the use of a triol with three primary hydroxyls (e.g., tris-hydrodroxymethyl ethane, THME) leads to formation of hyper-branched polymers. Regulating the ratio of glycerol to THME allows control of branching. The two-stage synthesis process disclosed herein can be used to control polycarbonate polyol molecular weights, degree of branching, and hydroxyl content, which are crucial parameters for biomedical, and/or high performance coating applications.

This application discloses the synthesis of random aliphatic poly(carbonate-co-esters) from conventional monomer feeds (e.g., diethyl carbonate, aliphatic diester and diol) under mild reaction conditions (60-95° C.) using a metal-free enzyme catalyst. The ratio of carbonate and ester repeating units is adjustable over a wide range, i.e. from 15:85 to 85:15 mol/mol. The synthesized, random poly(butylenecarbonate-co-butylenesuccinate), poly(BC-co-BS), copolymers possess higher thermal stability than poly(butylenecarbonate), but are less thermally stable than poly(butylenesuccinate). The morphology of these copolymers varies from semi-crystalline to near completely amorphous as a function of the polymer composition selected. Presence of only one crystal phase (either of the PBC-type or the PBS-type) found in poly(BC-co-BS) copolymers indicates the inability of both crystal lattices to host the foreign comonomer units. Results of process-variable studies demonstrated effective methods to control the end group structures of the copolymers, and allowed preparation of predominantly hydroxyl-terminated macromers.

Aliphatic poly(carbonate-co-ester) diols are important intermediates for the production of new polyurethanes with tunable properties. The transesterification between an aliphatic polycarbonate and polyester represents a novel, alternative method for synthesizing both random and block poly(carbonate-co-esters). This invention also demonstrates that within a specific range of BC/BS unit ratios, poly(BC-co-BS) copolymers have strong adhesive properties. This demonstrates that aliphatic poly(carbonate-co-esters) can be used as biodegradable adhesives.

In addition, this invention discloses a method that allows the direct preparation of aliphatic polycarbonates to high molecular weights with excellent control of end-group structure as well as with low polydispersity ($\leq 2.0$) without fractionating the product by precipitation into a non-solvent or any other fractionation method. Aliphatic polycarbonates (e.g., PBC and POC) with $M_w$ up to 29 000 were prepared via copolymerization of dialkyl carbonate with diols. The end-group structures of the polymers were regulated using the following two methods: (1) adjusting the dialkyl carbonate/diol monomer ratio; and (2) adding reduced sugars (alditols) as promoters. The former was conveniently used to prepare low molecular weight ($M_n \leq 10\,000$) hydroxyl-terminated polycarbonates and polymers with high alkyl carbonate end group content (>95 mol-%). The latter was remarkably effective in synthesizing high molecular weight ($M_n \geq 10\,000$) polycarbonate diol macromers.

Furthermore, it was also discovered that aliphatic polycarbonate chains containing alkyl carbonate end groups can be selectively converted in the presence of N435 catalyst to corresponding polycarbonate diols via reaction with a hydrogenated sugar, such as D-mannitol. This method for selective modification of polycarbonate chain end groups can be extended to a range of other aliphatic polycarbonate structures, such as those described in the literature prepared using organometallic catalysts. Polycarbonates with functional end groups, such as hydroxyl, are important building blocks for synthesizing various useful copolymers containing polycarbonate segments.

BRIEF DESCRIPTION OF THE FIGURES

Other features and technical advantages of the present invention will become more apparent from a study of the following description and the accompanying drawings, in which.

DETAILED DESCRIPTION OF PREFERRED EMBODIMENTS

Definitions

In this specification, various terms are defined as follows:

"Regioselective reactions" are reactions in which at least two constitutional isomers can be formed from a single reactant but one isomer is observed to be the predominant product of the reaction. Regioselective reactions can also include reactions in which one isomer is formed exclusively. In this invention, it refers primarily to the selective condensation of one or more hydroxyl groups contained within a polyol that has 3 or more hydroxyl groups.

"Chemical reactions" can include the formation or dissociation of ionic, covalent, or noncovalent structures through known means. Chemical reactions can include changes in environmental conditions such as pH, ionic strength, and temperature. For example, suitable chemical reactions for this invention involve the formation of ester bonds between terminal chain units containing an alkyl carbonate and hydroxyl groups. Alternatively, suitable chemical reactions can occur between hydroxyl and ester groups on monomers or propagating chains.

"Bonds", "bonding", and "linkages" are ionic, covalent, or noncovalent attractions of all types.

A "polymer" comprises homopolymers, copolymers, and combinations thereof. Polymers normally refer to chains of monomers with at least 10 monomeric repeat units.

A "diol" can be any compound in which there are two hydroxyl groups.

A "triol" can be any compound in which there are three hydroxyl groups.

Unless otherwise defined, all technical and scientific terms used herein have the same meaning as commonly understood by one of ordinary skill in the art to which this invention pertains. Although methods and materials similar or equivalent to those described herein can be used in the practice and testing of this invention, suitable methods and materials are described below. In addition, the materials, methods, and examples are illustrative only and not intended to be limiting.

Preferred Embodiments

One embodiment of this invention is a scalable method for enzyme-catalyzed copolymerization of carbonates (e.g., diethyl carbonate) and aliphatic diesters with alcohols. This method can be used to prepare poly(carbonate-co-ester) through the use of enzymes. Routes to high-purity poly(carbonate-co-ester) products can be beneficial for medical materials in various forms (films, molded parts, particles of various sizes, e.g. micron or nano-dimensions), macromers for polyurethane synthesis, intermediates for coating formulations, electronic material applications as well as other technical fields.

Figure 1:
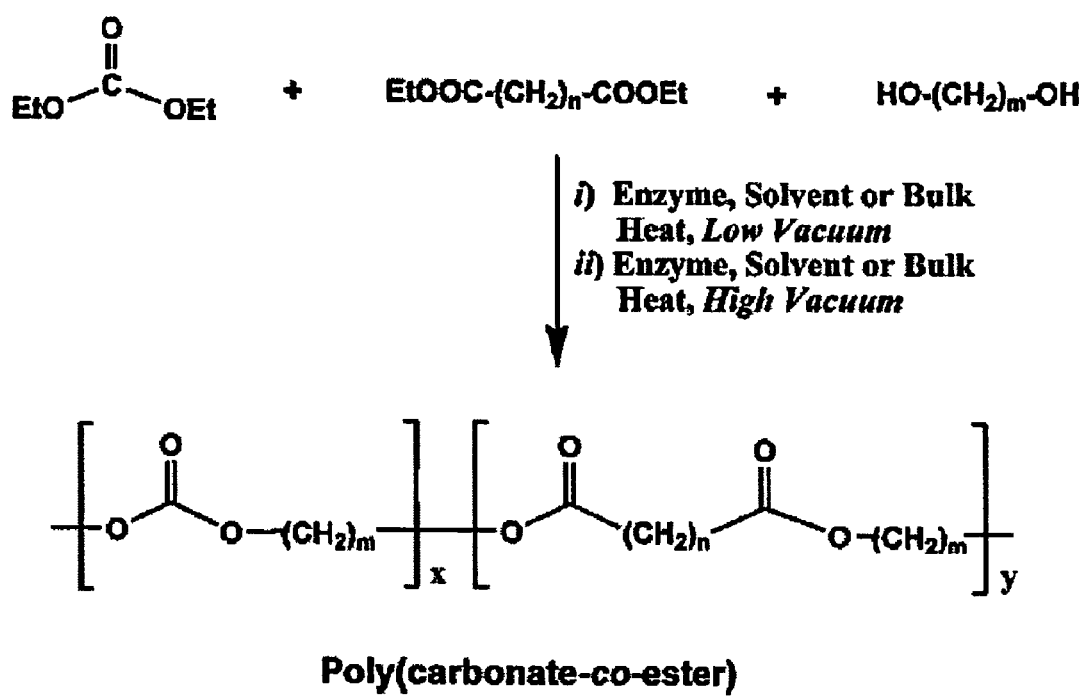
FIG. 1 is a schematic of a two-stage process for terpolymerization of diethyl carbonate (DEC), aliphatic diester and a diol.

The embodiment of this invention is a method for the preparation of polymers via catalyzed esterification of a mixture of selected reactants. This reaction can proceed as a two-stage process for terpolymerization characterized by a first stage reaction where monomers are converted to oligomers and a second stage reaction where the oligomers are converted to polymers. FIG. 1 depicts a representative reaction for aliphatic poly(carbonate-co-ester) synthesis from DEC, diester and diol. This method can be used to vary the molecular weights, the degree of branching, content of pendant hydroxyl groups along chains and composition of chain end groups. This method can utilize a terpolymerization enzymatic polycondensation reaction comprising the steps of:

(1) selecting reactants such that a first reactant is a dialkyl carbonate, a second reactant is an aliphatic diester, and a third reactant is a aliphatic diol or triol;
(2) selecting a catalyst from a family of those that catalyze various ester hydrolysis reactions in aqueous environments;
(3) adding the catalyst to the reaction mixture and allowing polymerization to proceed; and
(4) isolating the product polymer.

As discussed earlier, this method can make use of at least three (3) types of reactants:

The first reactant can be a dialkyl carbonate of the formula:

$$CO(OR)_2 \qquad (1)$$

wherein R represents straight-chain or branched C1-C5-alkyl ($C_nH_{2n+1}$). The most effective dialkyl carbonates, to which preference is consequently given, are those in which the alkyl groups comprise no more than five carbon atoms. Examples of such dialkyl carbonates, are dimethyl, diethyl, di(n-propyl), di(n-butyl), di(sec-butyl), diisobutyl, di(tert-butyl), di(n-pentyl), diisoamyl, and dineopentyl carbonates.

The second reactant can be an aliphatic diester of the formula:

$$R-((CO)-R1)_2 \qquad (2)$$

wherein the R-group represents a generalized group. The R-group as shown in Formula 2 comprises between 1 and 30 carbon atoms. The R-group can contain various degrees of unsaturation (CH=CH) where alkene groups are isolated or conjugated. Further, the R-group can be unsubstituted and represented generally as $-(CH_2)_n-$. The R-group can have one or more unsaturated groups that are isolated or conjugated. The presence of double bonds can result in a cis or trans configuration. Further, the R-group can have at least one triple bond. When the group has more than one double or triple carbon-carbon bond or combination thereof, these bonds can be conjugated or non-conjugated.

Further, the R groups can have a hydrocarbon-based backbone and the carbon atoms may be replaced by hetero atoms, e.g., S, O, N or Se. The carbon atoms can also be replaced by aromatic moieties such as phenyl, napthyl and anthracine moieties. Aromatic moieties can have other substituents such as hydroxyl and methoxy groups. The R-group R can be a linear or branched hydrocarbon group having 3-10 carbon-atoms; the diester can be selected from the group comprising linear or branched C4-C8 diacids. Also a mixture of diesters can be used as well. Hydrogens of methylene groups along hydrocarbon chains can be substituted with halogens such as chlorine, fluorine, and bromine. One example includes diacids containing $-(CF_2)_n-$ segments where n can be from 1 to 12. Also, diesters can contain silicone $[Si(CH_3)_2-O-Si(CH_3)_2]_x$ segments, where x can be from 1 to 30.

The third reactant can be an alcohol (e.g., aliphatic diols/triols). In certain situations, the third reactant can be an aliphatic diol of the formula:

$$HO-R-OH \qquad (1A) \qquad (3)$$

Aliphatic diols can have between 2 to 10 carbon atoms, such as 1,2-ethanediol, 1,3-propanediol, 1,4-butanediol, 1,6-hexanediol, 1,5-pentanediol, 1,10-decanediol, 2-methyl-1,3-propanediol, 2-methyl-2-butyl-1,3-propanediol and 2,2-dimethyl-1,4-butanediol, neopentylglycol hydroxypivalate, diethylene glycol, triethylene glycol, and methyldiethanolamine. The R-group of the third reactant can be flexible and be of the type disclosed above, in connection with diester. Alternatively, the third reactant can include triols that have at least two primary hydroxyl groups. For more extensive branching, the triol can have three or more primary hydroxyl groups. The use of a triol containing only two primary hydroxyls (e.g., glycerol) can result in formation of linear polycarbonate polyols, whereas the use of a triol with three primary hydroxyls (e.g., tris-hydrodroxymethyl ethane, THME) leads to formation of hyper-branched polymers. By regulating the ratio of glycerol to THME allows control of branching.

In another embodiment, copolymerizations would include a fourth component selected from the broad family of cyclic lactones. By this approach, carbonate units along chains would be formed by reactions between diols/triols and alkyl carbonates and ester repeat units can be formed by lactone ring-opening. Both lactone ring-opening and carbonate bond formation can occur by enzyme-catalysis: i) in the first step during prepolymer synthesis; ii) in the second step during polymer synthesis; or iii) during both prepolymer and polymerization steps. Thus, it is understood that formation of ester bonds during polyester-polycarbonate synthesis can occur by condensation between diols/triols and dialkyl esters, lactone ring-opening, or through a combination of both condensation reactions between diols/triols with diakyl diesters and lactone ring-opening. Suitable lactones for this work include s-caprolactone, para-dioxanone, glycolide, macrolacones (e.g. $\epsilon$-pentadecalactone) and other lactones that are well known in the practice of preparing polyesters by enzyme-catalyzed lactone ring-opening polymerizations.

In another embodiment, a transesterification between aliphatic polycarbonate and polyester can provide a method for synthesizing both random and block poly(carbonate-co-esters). For example, aliphatic poly(carbonate-co-esters) could be synthesized by a transesterification of an aliphatic polycarbonate with polyester using a CALB catalyst. This method allows for the direct preparation of aliphatic polycarbonates comprising high molecular weights, control of end-group structures, average block lengths of polyester and polycarbonate segments of 2.8, and polydispersity<2.0.

The lipase can be used to catalyze inter-chain transesterification or transacylation reactions between preformed polycarbonate and polyester chains that result in the formation of poly(carbonate-co-ester) products. By extending the reaction time, the average block lengths of ester and carbonate segments can be shorter until, eventually, poly(carbonate-co-ester) products with random sequences can be formed. During such transesterification or transacylation reactions between polycarbonates and polyesters, the final composition of polymers with respect to ester and carbonate units can be determined by the ester/carbonate ratio of the preformed polymers used for enzyme-catalyzed transacylation reactions.

The end-group structures of the polymers can be regulated using at least the following two methods:
 (1) by adjusting dialkyl carbonate/diol monomer ratio, and
 (2) by adding reduced sugars (alditols) as promoters.

The former was used to prepare low molecular weight (e.g., $M_n \leqq 10\,000$) hydroxyl-terminated polycarbonates and polymers with high alkyl carbonate end group content (e.g., >95 mol-%). The latter was remarkably effective in synthesizing high molecular weight (e.g., $M_n > 10\,000$) polycarbonate diol macromers.

The terpolymerization or transesterification of the selected reactants can be catalyzed by enzymes that fall within the family of those that are active for ester hydrolysis in aqueous media. Such enzymes can be useful for catalysis of polycondensation reactions of the mixture because such enzymes can catalyze the formation of ester and carbonate bonds with or without the addition of solvent, under mild reaction conditions. Hydrolytic enzymes suitable with the present method include enzymes selected from the group comprising lipases, proteases, esterases and cutinases. The reaction proceeds for a period of time sufficient to allow ester and carbonate bond formation to occur.

Various enzymes are suitable for use with this invention. Lipases, such as *Candida antarctica* Lipase B (CALB) (manufactured by Novozyme or obtained by another source), *Mucor meihei* Lipase 1M, *Pseudomonas cepacia* Lipase PS-30, *Pseudomonas aeruginosa* Lipase PA, *Pseudomonas fluoresenses* Lipase PF, *Aspergillus niger* lipase, *Candida cylinderacea* lipase, and lipase from porcine pancreatic lipase can be used with this method. Cutinases, such as that from *Humilica insolens*, can be used with this method. Variants of these enzymes, generated by standard protein engineering methods such as error-prone PCR and gene shuffling, well known to those of ordinary skill in the art, can also be used with this method. Other enzymes suitable with this method can be obtained by commonly used recombinant genetic methods such as error-prone PCR, gene shuffling, and by mathematical multivariate statistical techniques. The later allows modeling of protein sequence-function relationships to guide evolutionary process where beneficial diversity is identified for further protein optimization. These, and other protein engineering strategies that are well known to those of ordinary skill in the art, also can be used with this method. Other enzymes suitable with this method can be obtained by commonly used recombinant genetic methods, as are described above. Furthermore, other suitable enzymes may be obtained from other commercial sources, identified by searches of gene data banks based on homology to known enzymes, isolated from organisms that produce such enzymes, or by the mining of DNA from various environments such as in soil.

The enzyme can be added to the mixture in a dried state to catalyze the formation of ester and/or carbonate bonds between the monomers, and propagating chains during polycondensation polymerizations. Alternatively, the enzyme can be added in an aqueous solution and the water subsequently can be removed under vacuum. Some water in the reactions is desirable and every enzyme-catalyzed reaction will have an optimal water content that should be retained in the reaction mixture to achieve optimal reaction kinetics. Such enzymes used in the process of the present invention may be bound on an inert carrier, for instance a polymer such as an anion exchange resin or an acrylic (e.g., crosslinked poly(methylmethacrylate), crosslinked poly(styrene) macroporous resins. Other such inert carriers include polypropylene, silica, polyester, or polyurethane resin. When the enzyme is bound on an inert carrier it can easily be removed from the reaction mixture without the need for a purification steps. Enzymes can be bound by physical adsorption or chemical coupling. Further, it is known that enzymes, such as CALB, can be used either in immobilized or non-immobilized form.

The enzyme may be present in the reaction vessel until the reaction reaches a desired completion. If the enzyme remains in the vessel for an excessive amount of time, the product formed may be further altered by the enzyme resulting in chain degradation, further chain build-up, and/or transesterification. Another possibility is that after excessive reaction times the enzyme can catalyze crosslinking reactions. The enzyme can be removed from the reaction mixture at any time during the reaction. In some instances, the enzyme recovered from the product had residual activity and can be re-used in subsequent polycondensation reactions to prepare polycarbonates and poly(carbonate-co-ester) products.

To drive the reaction to completion, it may be necessary to remove water and/or the alcohol (e.g., ethanol when using diethylcarbonate) that is evolved during the condensation reaction. Water and/or ethanol can be removed from the reaction through numerous techniques well established in the art. For example, the water/ethanol byproduct of condensation reactions can be removed by reducing the pressure or applying a vacuum. Alternatively, water and/or ethanol can be removed with a wiped film evaporator under reduced pressure. In another alternative method a desiccant such as a molecular sieve is used, taking precautions to avoid physical damage to supported enzymes due to abrasion between the desiccant and the enzyme support. Another alternative can include passing dry air or nitrogen into the reaction mixture so that water and/or ethanol is transferred from the reaction mixture to the air that subsequently leaves the reaction vessel.

The reaction in this method can be quenched by means understood by persons of ordinary skill in the art. For example, the quenching of the reaction can be accomplished by removal of the enzyme from the reaction by a filtration step. To aid in the filtration, minimal amounts of a solvent such as methanol can be added to reduce the viscosity of the product mixture during the filtration process. In some cases the removal of the enzyme can be accomplished by filtration without addition of a solvent. In another alternative, the enzyme can be affixed to the walls of the reactor or a fixed bed column. Thus, removal of the product from the reactor or column results in separation of the enzyme and quenching of the reaction.

In some instances, when no solvent is added during separation of the product from the catalyst, the obtained product can be used directly. Alternatively, after the reaction is quenched, the polymer product can be precipitated by cooling the reaction mixture and/or adding a non solvent such as methanol. An alternative method is the use of filtration methods. For example, after separation of the enzyme as above, unreacted low molar mass compounds (e.g., polyols) can be removed by filtration using a low molecular weight cut-off membrane (e.g. <5 000 Kda). Removal of residual water-soluble low molar mass compounds can be achieved by washing the product with water. Thus, the high molecular weight polycarbonate or poly(carbonate-co-ester) will be retained during the filtration. To reduce the viscosity of the product during the filtration, the addition of a safe solvent such as supercritical carbon dioxide may be useful. For some applications, removal of unreacted substances from the product may not be necessary.

The progression of the reaction can be monitored at any time during the reaction. One method to monitor the progress of the reaction is by withdrawing a portion of the reaction mixture. The portion can be analyzed by techniques such as NMR spectroscopy and GPC (gel permeation chromatography) chromatography. Other methods to test the progression are known to those with ordinary skill in the art.

The total reaction time is generally from about 30 minutes to greater than 48 hours. It should be noted that during reactions in non-aqueous media some enzymes can denature at temperatures significantly higher than 90° C. and that some enzymes may only allow the reactions to proceed relatively slowly. Furthermore, by reduction in reaction temperatures can lead to increases in reaction viscosity that increase diffusional constraints and slow reactions.

The reactants can be heated to specific temperatures, or through a range of temperatures. For example, the reactants can be heated to a temperature in the range and held at that temperature for a period of time, or for a time sufficient to allow the reaction to proceed to a desired completion. In another example, the reactants can be heated through a range of temperatures within the temperature range, either randomly or in a pattern. For another example, the reactants can be heated to a first temperature within the temperature range, held at that first temperature for a period of time, then heated to a second temperature within the temperature range, and held at that second temperature for a period of time. This procedure can be continued or varied achieve the most effective esterification reaction.

It is understood to one skilled in the art that the present method can be used to form products that are not crosslinked as well as products with a tailored degree of crosslinking. In some cases, a certain extent of crosslinking may be desired. In other applications of this invention, the desired outcome is a higher degree of selectivity where little or no crosslinking occurs during the enzymatic esterification between dialkyl carbonates, polyols and diesters. Both little or no crosslinking and the tailoring of certain crosslinking levels can be achieved by this invention. The elimination or introduction of crosslinks will be a function of the enzyme used, the reaction conditions (e.g., reaction time, temperature) and the substrates. The reactions can be tuned to achieve higher or lower selectivity.

Polymers resulting from this method may include polymers with one, two or more repeating units that are distributed randomly, alternating, in blocks, or combining different elements of these arrangements. The polymers may all be of the same molecular weight, have a distribution of molecular weights that are narrow or broad, and be combinations of relatively short chains or individual species.

This method generally enables the preparation of both low and high molar mass polycarbonates and poly(carbonate-co-ester) that have a desired fraction of their side groups with hydroxyl moieties. Furthermore, these products can be prepared in both low and high molecular weights with high (>90%) contents of hydroxyl end groups or (>95 mol) alkyl carbonate end groups. The former, with high hydroxyl end group content as well as hydroxyl pendant groups along chains, can be remarkably effective in synthesizing higher molecular weight polycarbonate macromers.

In another embodiment, aliphatic polycarbonate chains containing alkyl carbonate end groups can be selectively converted in the presence of N435 catalyst to corresponding polycarbonate diols via reaction with a hydrogenated sugar, such as D-mannitol. This method for selective modification of polycarbonate chain end groups can be extended to a range of other aliphatic polycarbonate structures, such as those prepared using organometallic catalysts. Polycarbonates with functional end groups, such as hydroxyl, are important building blocks for synthesizing various useful copolymers containing polycarbonate segments.

In another embodiment, copolymerizations would include a fourth component selected from the broad family of cyclic lactones. By this method, carbonate units along chains would be formed by reactions between diols/triols and alkyl carbonates and ester repeat units can be formed by lactone ring-opening. Both lactone ring-opening and carbonate bond formation can occur by enzyme-catalysis: i) in the first step during prepolymer synthesis; ii) in the second step during polymer synthesis; or iii) during both prepolymer and polymerization steps. Thus, it is understood that formation of ester bonds during polyester-polycarbonate synthesis can occur by condensation between diols/triols and dialkyl esters, lactone ring-opening, or through a combination of both condensation reactions between diols/triols with diakyl diesters and lactone ring-opening.

In another embodiment, the synthesis of random aliphatic poly(carbonate-co-esters) could be derived from conventional monomer feeds (e.g., diethyl carbonate, aliphatic diester and diol) under reaction conditions (60-95° C.) using an enzyme catalyst. The ratio of carbonate and ester repeating units is adjustable over a wide range, i.e. from 15:85 to 85:15 mol/mol. The synthesized, random poly(butylenecarbonate-co-butylenesuccinate), P(BC-co-BS), copolymers possess higher thermal stability than poly(butylenecarbonate), but are less thermally stable than poly(butylenesuccinate). The morphology of these copolymers varied from semicrystalline to near completely amorphous as a function of the polymer composition selected. Presence of only one crystal phase (either of the PBC-type or the PBS-type) found in poly(BC-co-BS) copolymers indicates the inability of both crystal lattices to host the foreign comonomer units.

Example 1

Discussed herein is an enzyme-catalyzed polycarbonate polyol synthesis performed with monomer feeds. In this example, immobilized *Candida antartica* Lipase B (Novozym 435, N435, Novozymes) was employed as a catalyst for terpolymerization of dialkyl carbonate with aliphatic diol and a triol under mild reaction conditions (<100° C.) to form high purity, metal-free, polycarbonate polyols with $M_w$ up to 100 000. N435 can be highly regiospecific in catalyzing reactions with triol substrates, in which only primary hydroxyl groups react with dialkyl carbonate or alkyl carbonate end groups and participate in chain growth reactions during the terpolymerization.

Materials

Diethyl carbonate, diethyl succinate, diethyl adipate, 1,4-butanediol, 1,6-hexanediol, propyl propionate, and diphenyl ether, chloroform (HPLC grade), chloroform-d, and methanol were purchased from Aldrich Chemical Company. Novozym 435 (N435, specific activity 10,500 PLU/g) was a gift from Novozymes. Novozym 435 consists of *Candida Antarctica* Lipase B (CALB) physically absorbed within the macroporous resin Lewatit VPOC 1600 (poly[methyl methacrylate-co-butyl methacrylate], supplied by Bayer). N435 contains 10% CALB located on the outer 100 um of the 600 um average diameter Lewatit beads.

Instrumental Methods

H and C NMR spectra were recorded on a Bruker AVANCE 300 spectrometer of a Bruker AVANcE 500 spectrometer. The number and weight-average molecular weights, $M_n$, $M_w$ wt- and $M_w$, respectively, of polymers were measured by gel permeation chromatography using a Waters HPLC system equipped with a model 510 pump, a Waters model 717 autosampler and a Wyatt Optilab DSP interferometric refractometer with 500, 103, 104 and 105 A Ultrastyragel columns in series. Also, Trisec GPC software version 3 was used for calculations.

a. Procedure for N435-Catalyzed Terpolymerization of Diethyl Carbonate (DEC), Aliphatic Diester and Diol.

A reaction mixture comprises: (i) DEC, diester and diol monomers; and (ii) N435 catalyst that is dried at 50° C. under vacuum for 18 hours prior to use. The reaction was performed either in solution of diphenyl ether or in bulk using a parallel synthesizer connected to a vacuum line with the vacuum (±0.2 mmHG) controlled by a vacuum regulator. The reaction was carried out in two stages. First, the reaction was oligomerized, followed by polymerization. During a first stage, an oligomerization reaction was stirred at 50-100° C. under 600 mmHg pressure for 18-24 hours. Subsequently, the pressure was reduced to 1-5 mmHg, and the reaction continued for another 24-60 hours. Intermittently, samples were withdrawn and dissolved in HPLC grade chloroform, whereby the enzyme was removed by filtration. The filtrate containing whole products were analyzed by GPC using polystyrene standards to measure polymer molecular weights. In order to determine polymer structures, the samples were dissolved in chloroform-d. Finally, the resultant solutions were filtered to remove catalyst particles and analyzed by H and C NMR spectroscopy.

b. Terpolymerization of DEC, Diethyl Succinate (DES) and 1,4-Butanediol (BD) at Various Temperatures in Diphenyl Ether.

A reaction mixture comprises DEC/DES/BD in a 2:1:2 molar ratio with N435 at 10 wt % of the total monomer and diphenyl ether solvent at 10 wt % of the total monomer. The reaction was magnetically stirred at 60-95° C. under 600 mmHg pressure for 20 hours. The reaction pressure was reduced to 2.0 mmHg, and continued for 55 hours. Samples were taken during the second stage polymerization under 2.0 mmHg. Intermittently, samples were withdrawn and dissolved in both HPLC grade chloroform and chloroform-d solvents, whereby the enzyme was removed by filtration. The chloroform solutions were analyzed by GPC using polystyrene standards to measure the polymer molecular weights. The chloroform-d solutions were analyzed by H and C NMR spectroscopy to determine the polymer structures.

c. Bulk Terpolymerization of DEC, DES, and BD at Various DEC/BD-DES Monomer Ratios.

A reaction mixture comprises DEC, DES, BD and N435 (23 wt % in relation to BD). Various molar ratios of DEC/DES/BD were used such as 0.5:0.5:1, 0.6:0.5:1, 1.5:0.5:1 and 2:0.5:1. During the reaction, the reactants were magnetically stirred at 80° C. under 600 mmHg pressure for 22 hours. The pressure was reduced to 2.0 mmHg and the reaction continued for an additional 27 hours. Upon completion of the reactions, the formed polymers were dissolved in HPLC grade chloroform and chloroform-d solvents. Subsequently, the enzyme was removed via filtration. The chloroform solution was analyzed by GPC using polystyrene standards to measure polymer molecular weights. The chloroform-d solutions were analyzed by H and C NMR spectroscopy in order to determine the polymer structures, especially the end-group structures.

d. Terpolymerization of DEC, Diethyl Adipate (DEA) and 1,6-Hexanediol (HD) in Diphenyl Ether.

A reaction mixture comprises DEC/DEA/HD in a 2:1:2 molar ratio with N435 (10 wt % in relation to total moner) and diphenyl ether solvent (120 wt % in relation to total monomer) was magnetically stirred at 60-90° C. under 600 mmHg for 22 hours. Subsequently, the reaction was reduced to 2.0 mmHg and continued for another 69 hours. Samples were taken during second stage polymerization. Upon completion of the reaction, the formed copolymers were dissolved in HPLC grade chloroform and chloroform-d solvents. Subsequently, the enzyme was removed via filtration. The chloroform solution was analyzed by GPC using polystyrene standards to measure polymer molecular weights. The chloroform-d solutions were analyzed by H and C NMR spectroscopy in order to determine the polymer structures, especially the end-group structures.

e. N435-Catalyzed Transesterification between DEC and Propyl Propionate (PP).

The reaction was carried out by adding 5 g (42.3 mmol) DEC and 4.92 g (42.3 mmol) PP and 0.5 g N435 into a closed reaction flask equipped with a 5 psig pressure release valve.

The reaction was magnetically stirred at 80° C. for 30 hours. Samples were taken during the reaction and dissolved in chloroform-d. Subsequently, the enzyme catalyst was removed via filtration. The filtrates were analyzed by GC-MS as well as H and C NMR spectroscopy. The reaction synthesized ethyl propyl carbonate (EPC), ethyl propionate (EP), and dipropyl carbonate (DPC). The MW of EP, EPC and DPC are 102 Da, 132 Da and 146 Da, respectively.

f. N435-Catalyzed Transesterification between Poly(butylene carbonate), PBC, and Poly(butylene succinate), PBS.

The method was carried out according to the following steps:

The first step was PBC synthesis. Here, a reaction mixture containing DEC (4.06 g, 34.4 mmol), BD (1.55 g, 17.2 mmol), N435 (0.36 g), and diphenyl ether solvent (3.10 g) were magnetically stirred at 70° C. under 600 mmHg for 20 hours. The pressure was subsequently reduced to 2.0 mmHg and the reaction proceeded for another 52 hours. Upon completion, a small sample of PBC was analyzed by GPC and NMR spectroscopy. The PBC had a $M_w$=13 800, $M_w/M_n$=1.7.

The second step was PBS synthesis. Here, a reaction mixture containing DES (3.00 g, 17.2 mmol), BD (1.55 g, 17.2 mmol), N435 (0.46 g) and diphenyl ether solvent (9.10 g) was magnetically stirred at 95° C. under 600 mm for 20 hours. The pressure was subsequently reduced to 2.0 mmHg and the reaction proceeded for another 52 hours. Upon completion, a small sample of PBS was analyzed by GPC and NM spectroscopy. The PBS has a $M_w$=23 400, $M_w/M_n$=1.6.

The third step was PBC-PBS transesterification. Here, the reaction mixture containing PBC of the first step and PBS of the second step were combined. The combined mixture was magnetically stirred at 95° C. under 2.0 mmHg for 67 hours. Upon completion of the reactions, the formed polymers were dissolved in HPLC grade chloroform and chloroform-d solvents. Subsequently, the enzyme was removed via filtration. The chloroform solution was analyzed by GPC using polystyrene standards to measure polymer molecular weights. The chloroform-d solutions were analyzed by H and C NMR spectroscopy in order to determine polymer structures, especially the end-group structures.

Results and Discussion for Example 1

Two Step Process:

The two-step process for terpolymerization of DEC, aliphatic diester and diol is required because of the high volatility exhibited by DEC. The first step proceeds at a low vacuum to change monomers into non-volatile oligomers. The second step converts the oligomers to polymers under high vacuum. FIG. 1 depicts a general reaction for aliphatic poly(carbonate-co-ester) synthesis from DEC, diester and diol.

Temperature Effects

DEC, DES and BD terpolymerization were evaluated at various temperatures in diphenyl ether using a 2:1:2 molar ratio, respectively, and 10 wt % N435 in relation to the total monomer. A sample analysis of the first-stage oligomerization at 600 mmHg for 20 hours formed poly(carbonate-co-ester) oligomers with less than 2 000 via GPC analysis. NMR analysis revealed hydroxyl, ethyl ester, and ethyl carbonate end groups of the oligomers.

Figure 2A:
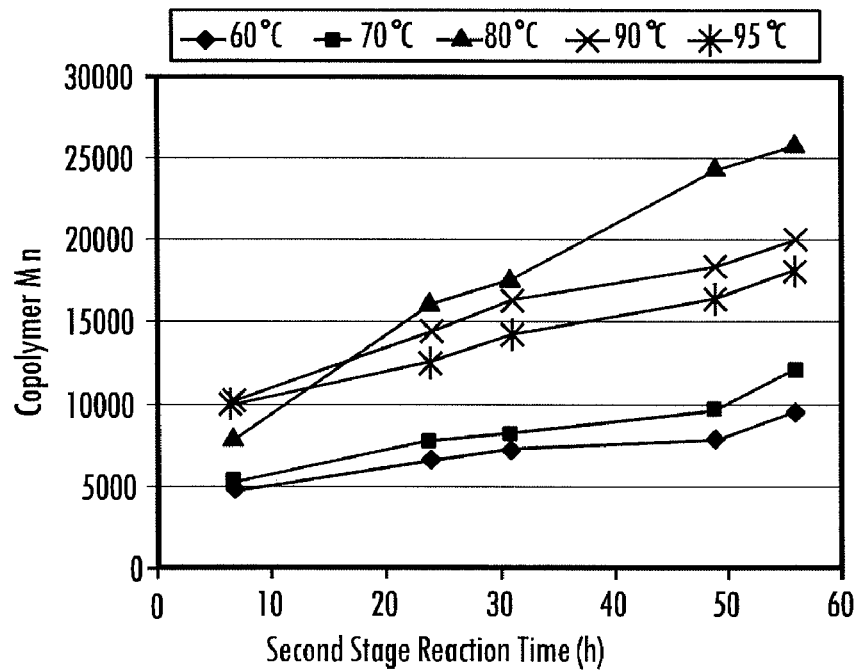
FIG. 2 illustrates the temperature effects on terpolymerization of DEC and diethyl succinate (DES) with 1,4-butanediol (BD) in diphenyl ether in a molar ratio of 2:1:2 DEC/DES/BD at 2.0 mmHg pressure. (A) depicts a graph of second stage reaction time versus molecular weight of the copolymer for various temperatures. (B) depicts a graph of the molecular weight of poly(butylene carbonate-co-butylene succinate) versus the polydisperity of the copolymer for various temperature ranges.
Figure 2B:
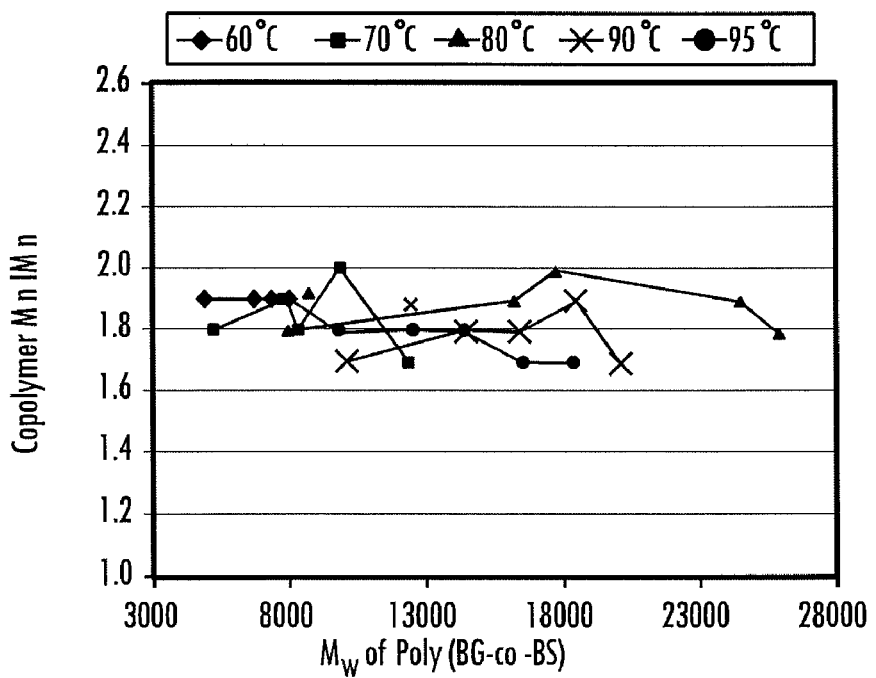

Chain growth versus reaction time was monitored during the second stage polymerization. FIG. 2A reveals that the molecular weight was between 5 000 and 10 000 after 6 hours for all reaction temperatures (i.e., 60, 70, 80, 90 and 95° C.). In particular, the reaction temperature of 80° C. exhibited typically higher molecular weights in relation to the other reaction temperatures at longer reaction times, especially upon completion. Namely, the molecular weight for the reaction temperature at 80° C. and 55 hours was 26 000. On the other hand, the molecular weights for 60, 70, 90 and 95° C. reaction temperatures at 55 hours was 9 800, 12 400, 20 200 and 18 400, respectively. FIG. 2B reveals the polydisperity ($M_w/M_n$) vs $M_w$, for poly(BC-co-BS) in relation to FIG. 2A at various temperatures. Copolymer polydisperities typically ranged between 1.7 to 2.0.

Figure 3:
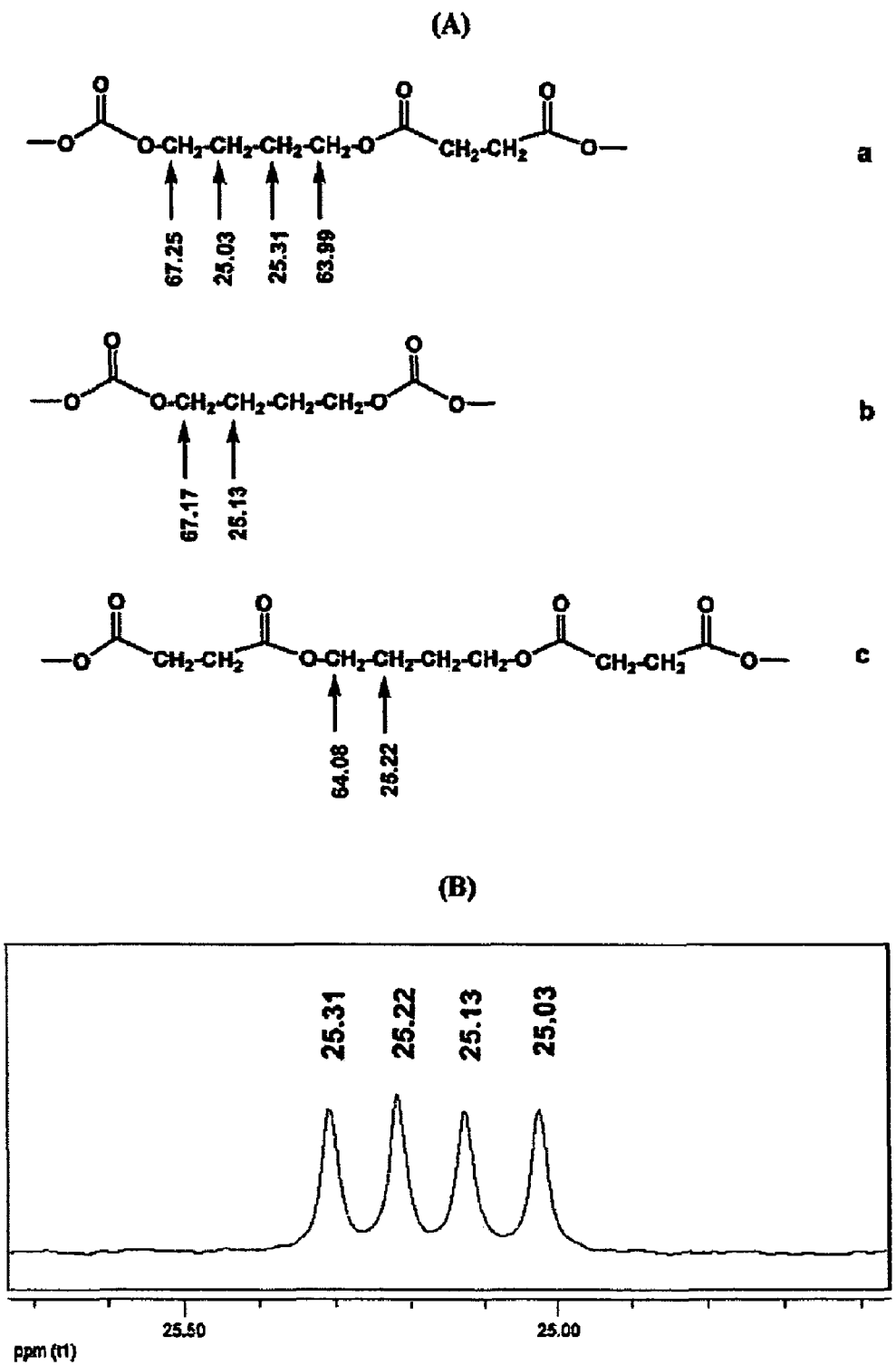
FIG. 3 illustrates selected carbon-13 resonance absorptions of poly(BC-co-BS). (A) depicts carbon-13 chemical shifts of tetramethylene groups in the copolymer. (B) depicts expansion of a carbon-13 NMR spectrum showing resonances of two middle tetramethylene carbons for poly(BC-co-BS) with 50:50 BC/BS unit ratio.

FIG. 3 illustrates a C NMR analysis of the distribution of BC and BS repeat units along polymer chains. Moreover, FIG. 3A provides chemical shifts for eight C NMR signals prepared at 80° C. for 55 hours in relation to three distinct tetramethylene groups as follows: (i) between carbonate and ester groups, (ii) between two carbonate groups, and (iii) between two ester groups. For (i), the four resonances listed from left to right are 67.25, 25.03, 25.31 and 63.99. For (ii), the two resonances from left to right are 67.17 and 25.13. For (iii), the two resonances are 64.08 and 25.22.

Additionally, FIG. 3A reveals the resonances of the two middle tetramethylene carbons for the poly(BC-co-BS) unit ratio. These values are derived from the middle values of the (i), (ii) and (iii) chains in FIG. 3A. Accordingly, a random distribution of BC and BS units in the copolymer are evident. Furthermore, random distributions were evident at all temperature ranges, particularly, 60, 70, 90 and 95° C. upon completion of 55 hours.

Figure 4:
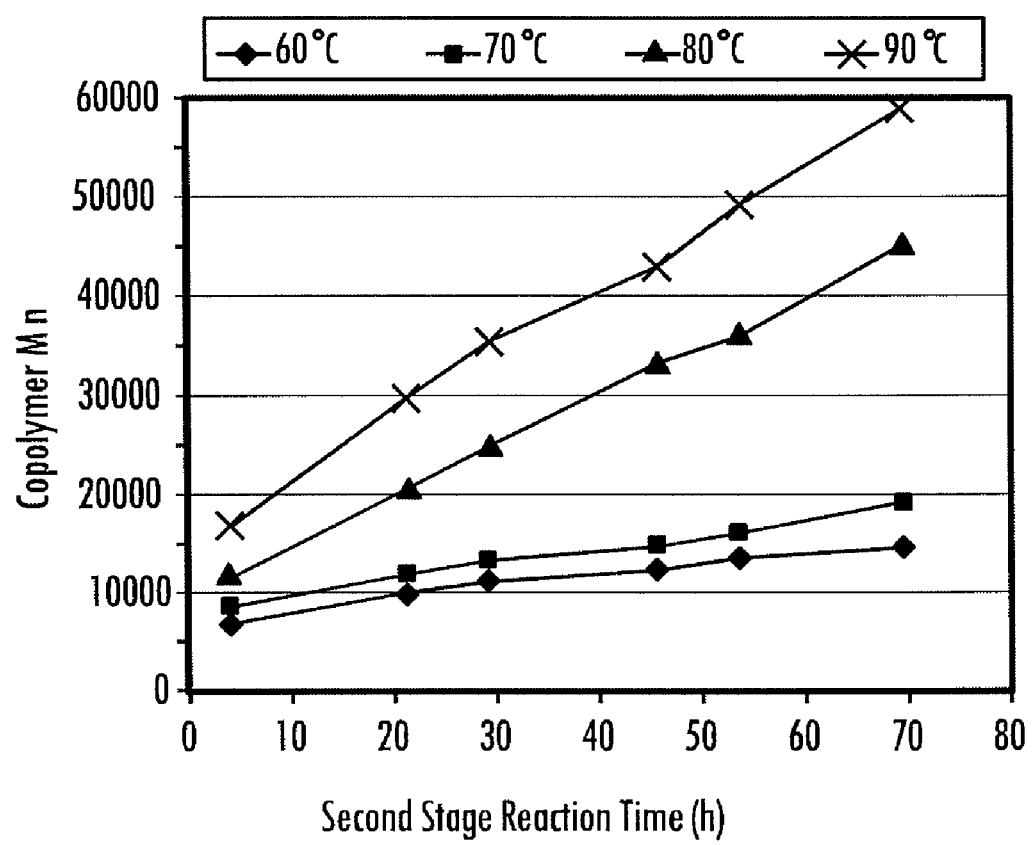
FIG. 4 illustrates the temperature effects on termpolymerization of DEC and DEA with HD in diphenyl ether (polymerization conditions: 2:1:1 molar ratio DEC/DEA/HD at 2.0 mmHg pressure.

In regard to the synthesis of poly(HC-co-HA), supra, utilizing DEC/DEA/HD having a 2:1:2 molar ratio, FIG. 4 illustrates the relationship between polymer chain growth and reaction time for DEC/DEA/HD terpolymerization performed in diphenyl ether at 60, 70, 80 and 90° C. In contrast to poly(BC-co-BS) synthesis as depicted in FIG. 2A, the polymer chain growth in this instance occurred at faster rate as temperature increased. In fact, the molecular weight increased between 80-90° C. Moreover, the DEC/DEA/HD terpolymerization at 60, 70, 80 and 90° C. for 69 hours (i.e., completion) exhibited $M_w$ of 14 800, 19 400, 45 500, 59 400, respectively. The polydisperity, $M_w/M_n$, at these reaction temperatures were 1.5, 1.5, 1.5 and 1.6, respectively.

Thus, it was readily observed that carbonate-ester copolymerizations occur at a faster rate by increasing the building block chain length from C4 to C6. In addition, lipase catalysis can take place where CALB is selective in macromer building block chain lengths, leading to $M_w/M_n$ values typically around 1.5. This polydisperity is far lower than statistically random polycondensation reactions. The results indicate that CALB-catalyzed copolymerization reactions between DEC, diol and diester occur with chain selectivity. As such, poly (carbonate-co-ester) oligomers and polymers synthesized via the disclosed catalysts, herein, produce better defined chain lengths in relation to similar poly(carbonate-co-ester) oligomers and polymers.

Effects of Monomer Ratio

The effects of variations upon DEC/(BD-DES) monomer feed ratios during DEC/DES/BD terpolymerization were conducted. An emphasis upon poly(BC-co-BS) end-group structures was analyzed. In particular, the DEC/BD molar ratio was fixed at 0.5:1 and the DEC/ to (BD-DES) molar ratio was varied from 1:1 to 1.2:1, 2:1, 3:1 and 4:1.

Table 1, as provided below, shows repeat units ratios, molecular weights, polydisperity, and end-group structures of resulting copolymers. When the DEC to (BD-DES) molar ratio was varied from 1:1 to 1.2:1, 2:1, 3:1 and 4:1, the content of hydroxyl end-groups in polymer chains decreased accordingly from 96% to 94% (1:1), 21% (1.2:1), 15% (2:1) and 10% (3:1), respectively. Alternatively, the ethyl carbonate plus ethyl ester end groups in copolymers increased from 4% to 6%, 79%, 85% and 90%, respectively. Accordingly, a DEC to (BD-DES) molar ratio of 1:1 is most preferable. Also, as the ratio of DEC/(BD-DES) was increased above 2:1 a corresponding increase in the ratio of BC to BS units was evident.

The terpolymerization of BD for entries 1-5 in Table 1 are performed under the following conditions: bulk reaction; 23 wt % N4355 vs BD; first stage oligomerization: 80° C., 600 mmHg, 22 hours; and a second stage polymerization: 80° C., 2.0 mmHg.

Preparation of Poly(Bc-co-Bs) Via Transesterification of Poly(Butylene Carbonate) (PBC) with Poly(Butylene Succinate) (PBS)

Figure 7:
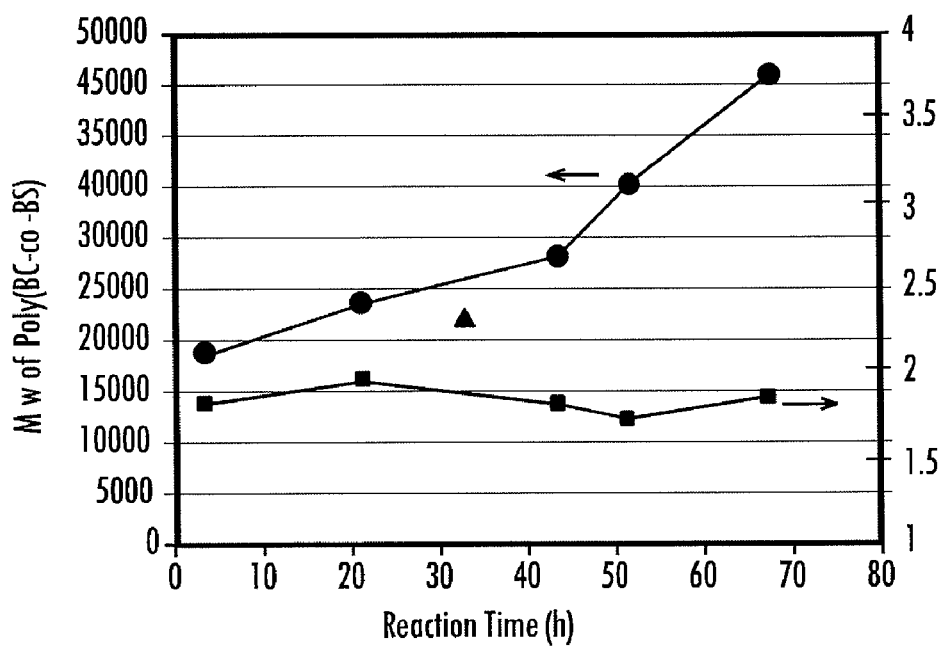
FIG. 7 illustrates a polymer molecular weight (Mw) and polydisperity (Mw/Mn) versus reaction time for Novozym 435-catalyzed transesterification between PBC and PBS in diphenyl ether (conditions: 95° C., 2.0 mmHg).

FIG. 7 shows a graph $M_w$ and $M_w/M_n$ as a function of reaction time. As time lapsed, $M_w$ increased. This is explained via an NMR analysis of polymers formed via a transesterification reaction between PBC and PBS. Here PBC and PBS initially generate poly(BC-B-BS) block polymers. As time increases, random poly(BC-co-BS) are produced. The molar ratio of PBC to PBS was 1:1 (17.2 mmol repeat units). Thus, the product was a block copolymer at 3 hour with PBC and

TABLE 1

Effects of Monomer Ratio on Termpolymerization of DEC, DES and BD

| entry | DEC/DES/BD (molar ratio) | BC/BS ratio | $M_n$ | $M_w/M_n$ | end group (mol %) —OH | —OC(O)OEt + —COOEt |
|---|---|---|---|---|---|---|
| 1 | 0.5:0.5:1 | 49:51 | 4600 | 2.0 | 96 | 4 |
| 2 | 0.6:0.5:1 | 50:50 | 5000 | 2.0 | 94 | 6 |
| 3 | 1:0.5:1 | 51:49 | 6900 | 2.0 | 21 | 79 |
| 4 | 1.5:0.5:1 | 55:45 | 5100 | 1.9 | 15 | 85 |
| 5 | 2:0.5:1 | 58:42 | 3700 | 1.8 | 10 | 90 |

N435-Catalyzed Transesterification between DEC and PP

Figure 5:
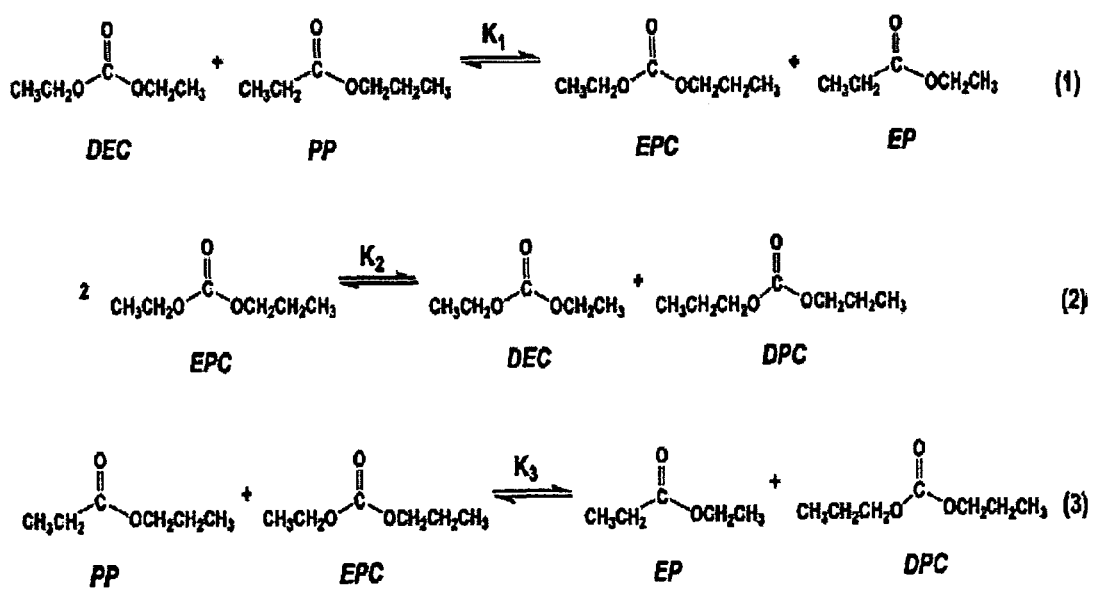
FIG. 5 illustrates an N435-Catalyzed transesterification starting from DEC and propyl propionate (PP).

FIG. 5 shows three equilibrium reactions coexisting during DEC/PP transesterification. Thus, during DEC/PP transesterification, DEC first undergoes transesterification with PP to form EPC and EP. See FIG. 5(i). Next, the synthesized EPC disproportionates to synthesize DEC and DPC as provided in FIG. 5(ii). In the alternative, synthesized EPC from FIG. 5(ii) may react with PP to form EP and DPC as provided in FIG. 5(iii).

Figure 6:
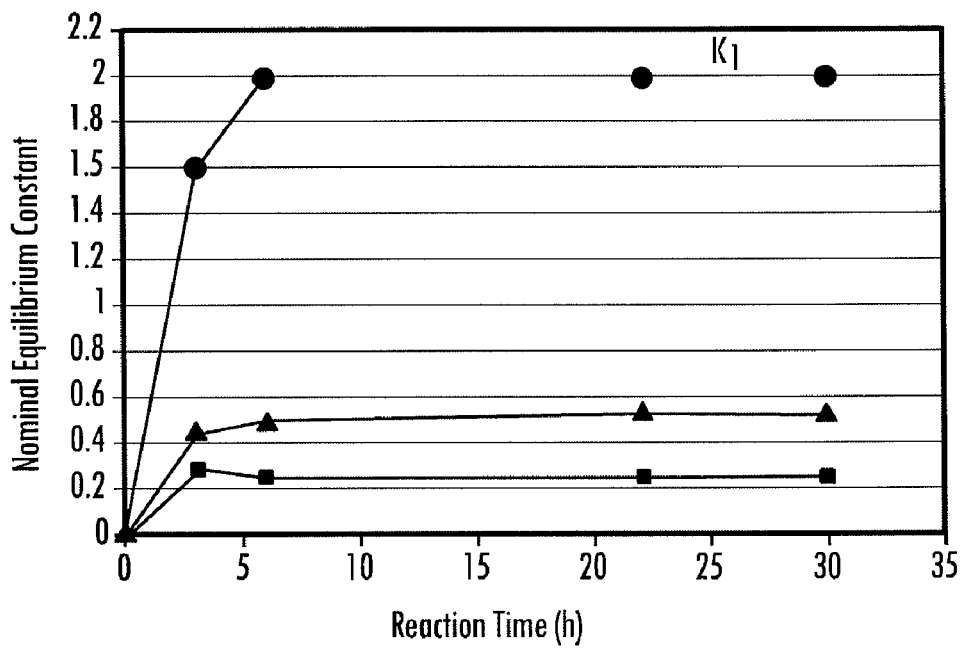
FIG. 6 illustrates nominal equilibrium constants versus reaction time for Novozym-435-catalyzed transesterifications starting from DEC and PP (conditions: 80° C., 1 atm, 5 wt % Novozym 435 versus total substrate).

FIG. 6 shows illustrates the nominal equilibrium constants k1, k2, k3 for reaction time. The DEC/PP transesterification was carried out at 80° C. using a 1:1 DEC/PP molar ratio as substrates. The equilibrium constants are defines as follows:

$$K_1 = ([EPC] \times [EP])/([DEC] \times [PP]) \quad (1)$$

$$K_2 = ([DEC] \times [DPC])/[EPC]^2 \quad (2)$$

$$K_3 = ([EP] \times [DPC])/([PP] \times [EPC]) \quad (3)$$

As provided in FIG. 6, carbonate-ester reactions have longer reaction times than carbonate-carbonate reactions to reach their equilibrium concentrations. Accordingly, the average maximum values of nominal $K_1$, $K_2$, and $K_3$ are 2.0, 0.27 and 0.52, respectively. See Table 2.

PBS segments having an average segment length of 2.8 repeat units. After 21 hours, random copolymers were achieved.

Example 2

Disclosed herein is the preparation of a series of poly(BC-co-BS) copolymers with BC/BS variable unit ratios. *Candida Antarctica* Lipase B (CALB) immobilized on Lewatit (Novozym 435) was used as catalyst to prepare poly(BC-co-BS) copolymers. The following discussion describes a method of obtaining desired physical properties of poly(carbonate-co-esters) by tuning poly(BC-co-BS) compositions through a selection of appropriate reaction conditions. Accordingly, the novel series of poly(BC-co-BS) polyols represent vital macromer building blocks for segmented polyurethane copolymer synthesis.

Materials

Diphenylmethane, Diethyl carbonate, diethyl succinate, diethyl adipate, 1,4-butanediol, 1,6-hexanediol, propyl propionate, and diphenyl ether, chloroform (HPLC grade), chloroform-d, and methanol were purchased from Aldrich Chemi-

TABLE 2

N435-Catalyzed Transesterification Reactions Starting from Diethyl Carbonate (DEC) and Propyl Propionate (PP) (Condition: 80° C., 1 atm, 5 wt % N435 vs Total Substrate)

| DEC/PP (mol/mol) | rxn time (h) | $[PP]^a$ | $[EP]^a$ | $[DPC]^c$ | $[EPC]^a$ | $[DEC]^c$ | $K_1^b$ (nominal) | $K_2^b$ (nominal) | $K_3^b$ (nominal) |
|---|---|---|---|---|---|---|---|---|---|
| 1:1 | 3 | 1.00 | 1.89 | 0.30 | 1.25 | 1.46 | 1.6 | 0.28 | 0.45 |
|  | 6 | 1.00 | 1.88 | 0.37 | 1.40 | 1.30 | 2.0 | 0.25 | 0.50 |
|  | 22 | 1.00 | 1.88 | 0.43 | 1.49 | 1.41 | 2.0 | 0.27 | 0.54 |
|  | 30 | 1.00 | 1.89 | 0.43 | 1.54 | 1.45 | 2.0 | 0.26 | 0.53 |
| 2:1 | 22 | 1.00 | 3.56 | 0.50 | 3.59 | 7.24 | 1.8 | 0.28 | 0.50 |
|  | 30 | 1.00 | 3.50 | 0.55 | 3.74 | 6.41 | 2.0 | 0.25 | 0.51 |

As discussed in Table 2, the molar concentrations of the starting reactants were determined by NMR spectroscopy, indicated by superscript 'a'. Moreover, superscript 'b' relates to corresponding equilibrium reactions provided in FIG. 5.

cal Company. Novozym 435 (N435, specific activity 10,500 PLU/g) was a gift from Novozymes. Novozym 435 consists of *Candida Antarctica* Lipase B (CALB) physically absorbed within the macroporous resin Lewatit VPOC 1600 (poly[methyl methacrylate-co-butyl methacrylate], supplied by Bayer). N435 contains 10% CALB located on the outer 100 um of the 600 um average diameter Lewatit beads.

Instrumental Methods

H and C NMR spectra were recorded on a Bruker AVANCE 300 spectrometer of a Bruker AVANCE 500 spectrometer. The number- and weight-average molecular weights, ($M_n$ and $M_w$, respectively) of polymers were measured by gel permeation chromatography (GPC) using a Waters HPLC system equipped with a model 510 pump, a Waters model 717 autosampler, and a Wyatt Optilab DSP interferometeric refractometer with 500, $10^3$, $10^4$ and $10^5$ Å Ultrastyragel columns in series. Also, Trisec GPC software version 3 was used for calculations. Thermogravimetric analysis (TGA) was carried out using a TA Instruments TGA2950 thermogravimetric analyzer from room temperature to 600° C., with a heating rate of 10° C./min, under nitrogen purge. Glass transition temperatures ($T_g$) were taken at the midpoint of the stepwise specific heat increment. Crystallization temperatures ($T_c$) and melting temperatures ($T_m$) were taken at the peak maximum of exotherm and endotherm, respectively. In cases where multiple endotherms are present, the temperature of high-T peak was taken as $T_m$. Differential Scanning Calorimetry (DSC) was also used in the temperature modulated mode (TMDSC), with heating rate=2° C./min, oscillation amplitude=0.5° C., and oscillation period=40 s. Wide-angle X-ray diffraction measurements (WAXS) were carried out at room temperature with a PANalytical X'Pert PRO diffractometer equipped with an X'Celerator detector (for ultrafast data collection). A Cu anode was used as X-ray source (K radiation: λ) 0.154 18 nm, 40 kV, 40 mA), and ¼° divergence slit was used to collect the data in 2θ range from 2° to 60°. After subtracting the diffractogram of an empty sample holder from the experimental diffraction curve, the amorphous and crystalline contributions in the resulting diffractogram were calculated by a fitting method using the WinFit program. The degree of crystallinity ($X_c$) was evaluated as the ratio of the crystalline peak areas to the total area under the scattering curve.

a. N435-Catalyzed Terpolymerization of Diethyl Carbonate (DEC), Diethyl Succinate (DES), and 1,4-Butanediol (BD).

In this example, copolymerization of DEC and DES with BD were performed either in solution or in bulk, in a parallel synthesizer. The reaction was vacuum controlled at 0.2 mmHg using a vacuum regulator. Reactions were conducted using various DEC/DES/BD monomer feed ratios illustrated in Table 3 and Table 4.

TABLE 4

Molecular Characterization and Molecular Weight Distribution of Homopolymers (PBS and PBC) and Poly(BS-co-BC) Copolymers

| product | DEC/DES/BD (molar ratio) | product yield[a] (%) | $M_w$ | $M_n/M_w$ |
|---|---|---|---|---|
| PBC[b] | | | 14 700 | 1.6 |
| poly(BC-co-14 mol % BS)[c] | 1.7:0.15:1 | 90 | 18 300 | 1.7 |
| poly(BC-co-29 mol % BS)[d] | 1.4:0.3:1 | 92 | 20 900 | 2.0 |
| poly(BC-co-50 mol % BS)[e] | | 95 | 59 400 | 2.1 |
| poly(BC-co-69 mol % BS)[f] | 0.6:0.7:1 | 94 | 19 700 | 1.6 |
| poly(BC-co-82 mol % BS)[f] | 0.3:0.85:1 | 95 | 18 800 | 1.7 |
| PBS[b] | | | 32 000 | 2.3 | b. Synthesis and Purification of Poly(BC-co-BS) Copolymers Used for Solid-State Characterizations.

In this example, monomer feed molar ratios of DEC to DES to BD were 1.7:0.15:1, 1.4:0.3:1, 0.6:0.7:1 and 0.3:0.85:1. Reactions with 0.6:0.7:1 and 0.3:0.85:1 DEC/DES/BD ratios were performed at 80° C. in diphenyl ether (140 wt % vs total monomer). Reactions with 1.7:0.15:1 and 1.4:0.3:1 DEC/DES/BD ratios were performed in diphenylmethane (50 wt % vs total monomer) at 70 and 80° C., respectively. All reactions at these four monomer ratios took place at 600 mmHg for 22 hours during first stage oligomerization and thereafter at 2 mmHg for 52 hours during second stage polymerization. Reaction temperature was maintained same during both stages. After completion of copolymerizations, reaction mixtures were dissolved in chloroform, and the resultant solutions were filtered to remove the enzyme catalyst. Filtrates with polymer products were concentrated under vacuum, and the resulting solutions were added drop wise to stirring methanol to precipitate copolymers. Products were isolated by filtration, washed on the filter pads with methanol three times, and dried at 50° C. under vacuum for 24 hours.

Results and Discussion for Example 2

Effects of Monomer Feed Ratio on Terpolymerizations of DEC with DES and BD.

Statistical analysis was conducted for synthesizing poly(BC-co-BS) with compositions other than 50:50 mol/mol BC to BS units. Experiments were conducted in diphenyl ether using 10 wt % N435 (vs to total monomer) at 80° C. Here, molar ratios of DEC/DES/BD in the monomer feed were 1.6:0.2:1, 1.2:0.4:1, 1.0:0.5:1, 0.8:0.6:1 and 0.4:0.8:1. The pressure and reaction time were 600 mmHg for 18 hours

TABLE 3

Effects of Monomer Ratio on Terpolymerization of DEC, DES and BD

| | | | | | | end group (mol %) | |
|---|---|---|---|---|---|---|---|
| entry | DEC/DES/BD (molar ratio) | BC/BS ratio | $M_w$ | $M_n$ | $M_w/M_n$ | —OH | —OC(O)OEt + —COOEt |
| 1 | 1.6:0.2:1[a] | 80:20 | 21200 | 13100 | 1.6 | 44 | 56 |
| 2 | 1.2:0.4:1[a] | 61:39 | 16300 | 9200 | 1.8 | 42 | 58 |
| 3 | 1.0:0.5:1[a] | 50:50 | 20200 | 11600 | 1.7 | 31 | 69 |
| 4 | 0.8:0.6:1[a] | 40:60 | 18300 | 9800 | 1.9 | 33 | 67 |
| 5 | 0.4:0.8:1[a] | 22:78 | 15800 | 8200 | 1.9 | 23 | 77 |
| 6 | 0.8:0.2:1[b] | 70:30 | 2300 | 1000 | 2.1 | 99 | 1 |
| 7 | 0.6:0.4:1[b] | 49:51 | 6500 | 3700 | 1.8 | 97 | 3 |
| 8 | 0.4:0.6:1[b] | 31:69 | 7800 | 4300 | 1.8 | 95 | 5 |
| 9 | 0.2:0.8:1[b] | 14:86 | 3700 | 2200 | 1.7 | 70 | 30 |
| 10 | 0.2:0.8:1[c] | 14:86 | 7300 | 3800 | 1.9 | 100 | 0 | during the first stage oligomerization and 2.0 mmHg for 53 hours during the second stage polymerization.

Figure 8:
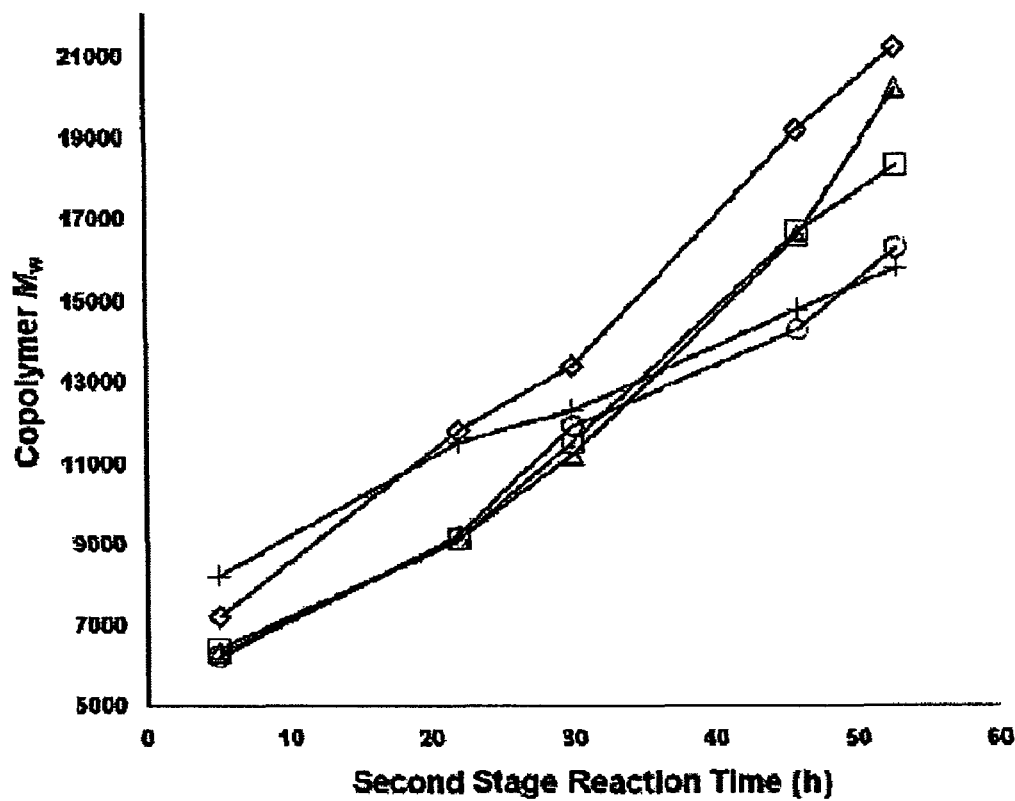
FIG. 8 illustrates the effects of DES/BD ratio on terpolymerization of DEC and DES with BD in diphenyl ether (polymerization conditions: 2:1 DEC/BD-DES), 80° C., 2.0 mmHg pressure): 0.2:1 DES/BD (◊), 0.4:1 DES/BD (○), 0.5:1 DES/BD (Δ-possible change with a real triangle), 0.6:1 DES/BD (□), 0.8:1 DES/BD (+).

FIG. 8 illustrates polymer chain growth vs polymerization time for copolymerizations conducted with different DES to BD feed ratios. Changes in the DES/BD ratio had no substantial effects on the polymerization rate. In all cases, $M_w$ increased continuously throughout terpolymerization reactions. Polydisperities ($M_w/M_n$) of synthesized poly(BC-co-BS) copolymers ranged between 1.6 and 1.9. In particular, using a monomer feed of 1.6:0.2:1 DEC/DES/BD, at 5, 22, 30, 46, and 53 hours resulted in the $M_w$ ($M_w/M_n$) values to be 7,200 (1.7), 11,800 (1.8), 13,400 (1.9), 19,200 (1.8), and 21,200 (1.6), respectively. In addition, when the monomer feed was 0.8:0.6:1 DEC/DES/BD, at 5, 22, 30, 46, and 53 hours, the corresponding $M_w$ ($M_w/M_n$) values were 6 400 (1.7), 9100 (1.8), 11 500 (1.8), 16 700 (1.7), and 18 300 (1.9), respectively.

With regard to Table 3, the first five entries of DEC/(BD–DES) were fixed at a 2:1 ratio. All products contained hydroxyl, ethyl carbonate, and ethyl ester terminal groups, although their relative content varied as a function of the monomer feed ratio. Comparison of the monomer feed ratios ([BD–DES]/[DES]) and copolymer compositions (BC to BS units) revealed that they are within a 2% deviation. As such, it can be appreciated that poly(BC-co-BS) composition is predetermined by selecting the desired monomer feed ratio.

Synthesis of Poly(BC-co-BS) Diols Using 1:1 DEC/(BD–DES) Ratio.

Poly(BC-co-BS) diols may be useful intermediates for producing specialty polyurethanes and other high molecular weight segmented copolymers. Accordingly, an analysis was performed where the DEC/(BD–DES) ratio was fixed at 1:1, but the DES-to-BD monomer feed ratio was varied.

In order to decrease diffusion constraints and thereby prepare poly(carbonate-co-esters) of higher molecular weight (e.g., $M_n$>10 000), terpolymerizations were performed in diphenyl ether. However, since commercial polyols often have molecular weights below 3 000, these terpolymerizations to prepare poly(BC-co-BS) polyols were performed in bulk.

In particular, entries 6-9 of Table 3 are discussed herein. In furtherance, values of $M_n$ ranged from 1 000 to 4 300, and end-group hydroxyl contents for entries 6, 7, and 8 are 99, 97, and 95, respectively. The BC-to-BS contents of copolymers in entries 6-9 were lower than corresponding DEC/DES monomer feed ratios. This is attributed to the loss of highly, volatile DEC during first stage oligomerization of the terpolymeriation reactions. The distribution of BC and BS units could not readily be determined due to overlap of carbon-13 resonances at 25.0-25.3 ppm between end-group (—CH2CH2CH2CH2OH) and main chain repeat units (—OCH2CH2CH2CH2O—). Nevertheless, the repeat units are also likely to be randomly distributed because the same reaction conditions exist here as provided during the DEC/DES/BD terpolymerization in diphenyl ether or diphenylmethane solution. The synthesis of random copolymers will be discussed below.

The relatively low terminal hydroxyl content (70%) of poly(BC-co-86 mol % BS) of entry 9 on Table 1 is likely derived from crystallization and phase separation of this copolymer from the reaction mixture. In order to overcome product solidification, terpolymerization using 0.2:0.8:1 molar ratio DEC/DES/BD under the same conditions as in the bulk reaction above was performed, except diphenylmethane (70 wt % versus total monomer) was used as a solvent in lieu of diphenyl ether. The addition of diphenylmethane to reactions resulted in monophasic solutions throughout polymerizations that prohibited polymer precipitation and crystallization. The results show that entry 10 exhibits a higher molecular weight by 1 600 with near perfect incorporation of hydroxyl terminal units.

Synthesis of Poly(BC-co-BS) for Solid-State Characterizations.

Table 4 shows a series of poly(BC-co-BS) copolymers with BC-to-BS unit ratios of 86:14, 71:29, 31:69, and 18:82 that were prepared and purified using corresponding DEC/DES/BD monomer molar ratios of 1.7:0.15:1, 1.4:0.3:1, 0.6:0.7:1 and 0.3:0.85:1, respectively. The reaction conditions were as follows: diphenylmethane (50 wt % versus total monomer); 10 wt % N435 (versus total monomer); first stage oligomerization: 70° C., 600 mmHg, 22 hours; and second stage polymerization: 70° C., 2.0 mmHg, 52 hours.

All copolymerizations at the four above-mentioned monomer ratios were initially performed in diphenyl ether to obtain polymer products with desirable molecular weights. However, subsequent analysis of products showed that while poly (BC-co-BS) copolymers with $\geqq$50 mol % BS unit contents could readily be separated from diphenyl ether via reprecipitation in chloroform/methanol, the experiment was unsuccessful in removing residual diphenyl ether (~10-20 wt %) from poly(BC-co-14 and 29 mol % BS) copolymers owing to their high affinity to this solvent.

This problem was solved by using diphenylmethane in place of diphenyl ether. By performing polymerizations in diphenylmethane, solvent-free poly(BC-co-29 and 14 mol % BS) copolymers were successfully prepared. Copolymers with 29, 69, and 82 mol % BS units were prepared in sufficiently high molecular weights (Mw$\geqq$15 000) by conducting reactions at 80° C. However, poly(BC-co-14 mol % BS) synthesis was performed at 70° C. in order to obtain the copolymer in sufficiently high molecular weight for subsequent solid-state analyses. To remove low molecular weight impurities and solvent, poly(BC-co-BS) products were precipitated in methanol. The yields of all precipitated polymers were greater than 90%.

The reference homopolymer and copolymer $M_w$ values in Table 4 ranged from 14 700 to 32 000, and their $M_w/M_n$ ranged from 1.6 to 2.3. An interesting observation from this experimentation was poly(BC-co-29 mol % BS) copolymer's remarkable adhesive properties toward various surfaces, such as stainless steel, glass, and natural wood.

Table 5 shows the distributions of diad structures for poly (BC-co-14 mol % BS), poly(BC-co-50 mol % BS), poly(BC-co-69 mol % BS), and poly(BC-co-82 mol % BS) copolymers. Experimental results of diad distributions, measured by 13C NMR absorptions, are in good agreement with those theoretically calculated for statistically random copolymers data. As such, random copolymers were formed regardless of BC or BS unit content in polymer chains, and comparisons of solid-state properties are based on random structures of these copolymers.

TABLE 5

Structures of Poly(BC-co-BS) Copolymers

| | BC-BS + BS-BC | | BC-BC | | BS-BS | |
| --- | --- | --- | --- | --- | --- | --- |
| sample | measd[c] | calcd[d] | measd[c] | calcd[d] | calcd[d] | measd[c] |
| poly(BC-co-14 mol % BS)[a] | 0.27 | 0.24 | 0.69 | 0.74 | 0.04 | 0.02 |
| poly(BC-co-50 mol % BS)[b] | 0.5 | 0.5 | 0.25 | 0.25 | 0.25 | 0.25 |

TABLE 5-continued

Structures of Poly(BC-co-BS) Copolymers

| sample | BC-BS + BS-BC | | BC-BC | | BS-BS | |
|---|---|---|---|---|---|---|
| | measd[c] | calcd[d] | measd[c] | calcd[d] | calcd[d] | measd[c] |
| poly(BC-co-69 mol % BS)[a] | 0.43 | 0.43 | 0.08 | 0.09 | 0.49 | 0.48 |
| poly(BC-co-82 mol % BS)[a] | 0.3 | 0.3 | 0.03 | 0.03 | 0.67 | 0.67 |

Thermal Characterization.

Figure 9:
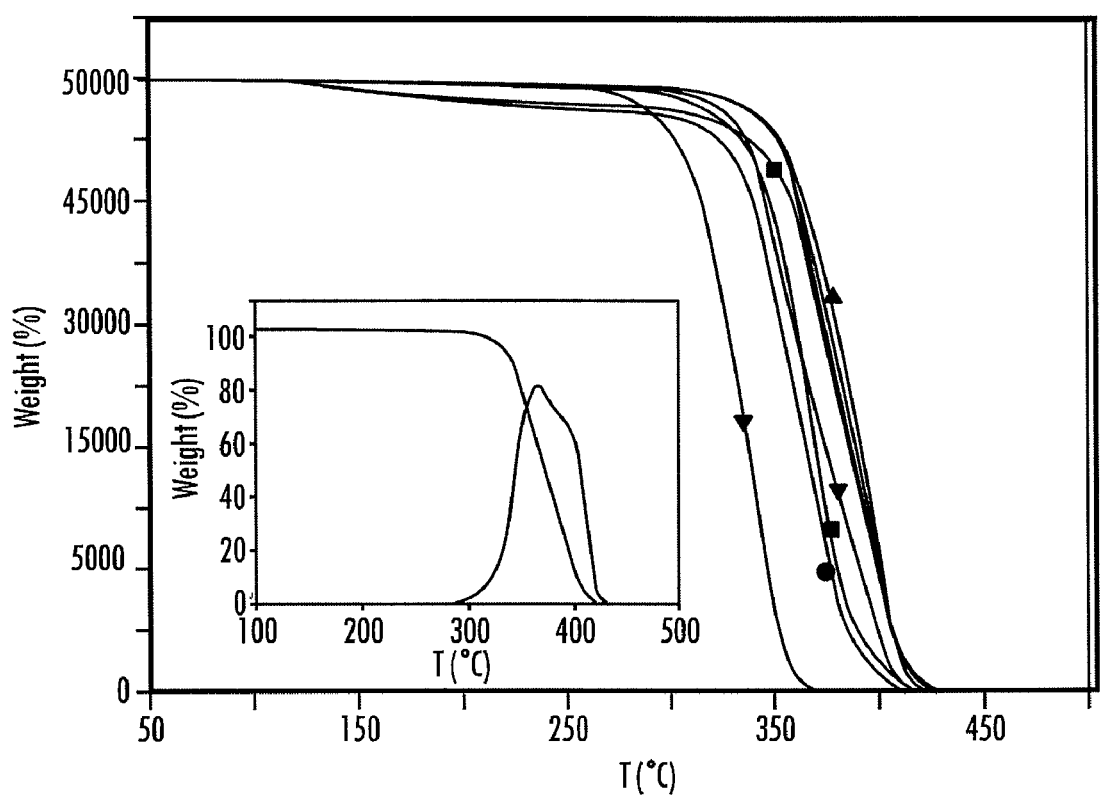
FIG. 9 illustrates thermogravimetric curves of: PBS (Δ), PBC (∇), poly(BC-co-82 mol % BS) (■), poly(BC-co-69 mol % BS) (○), poly(BC-co-50 mol % BS) (▲), poly(BC-co-29 mol % BS) (□), and poly(BC-co-14 mol % BS) (●). Inset: magnification of thermogravimetric (-) and derivative (--) curves of poly(BC-co-50 mol % BS).

FIG. 9 compares thermogravimetric curves of poly(BC-co-BS) copolymers with those of reference PBC and PBS homopolymers. As seen in the graph, PBC and PBS degrade in a single step centered at 338 and 391° C., respectively. Lower thermal stability of the polycarbonate is attributed to thermally induced decarboxylation reactions. Both homopolymers are completely decomposed at 600° C. The main weight loss of all copolymers in FIG. 9 lies between those of the two homopolymers. This observation suggests that the insertion of butylene succinate units in PBC chains hinders to some extent the degradation mechanism of PBC and that copolymerization with ester units may be used to raise the thermal stability of polycarbonates.

In addition, an inset of FIG. 9 shows a magnification of the thermogravimetric curve of poly(BC-co-50 mol % BS). A dual degradation behavior is observed in the derivative curve. Namely, although the higher temperature step occurs in the temperature range of plain PBS degradation, NMR analysis from Table 3 rules out the presence of PBS blocks in this copolymer. The origin of the observed dual degradation behavior in poly(BC-co-50 mol % BS) remains unclear given that all copolymers are completely decomposed at 600° C.

Figure 10:
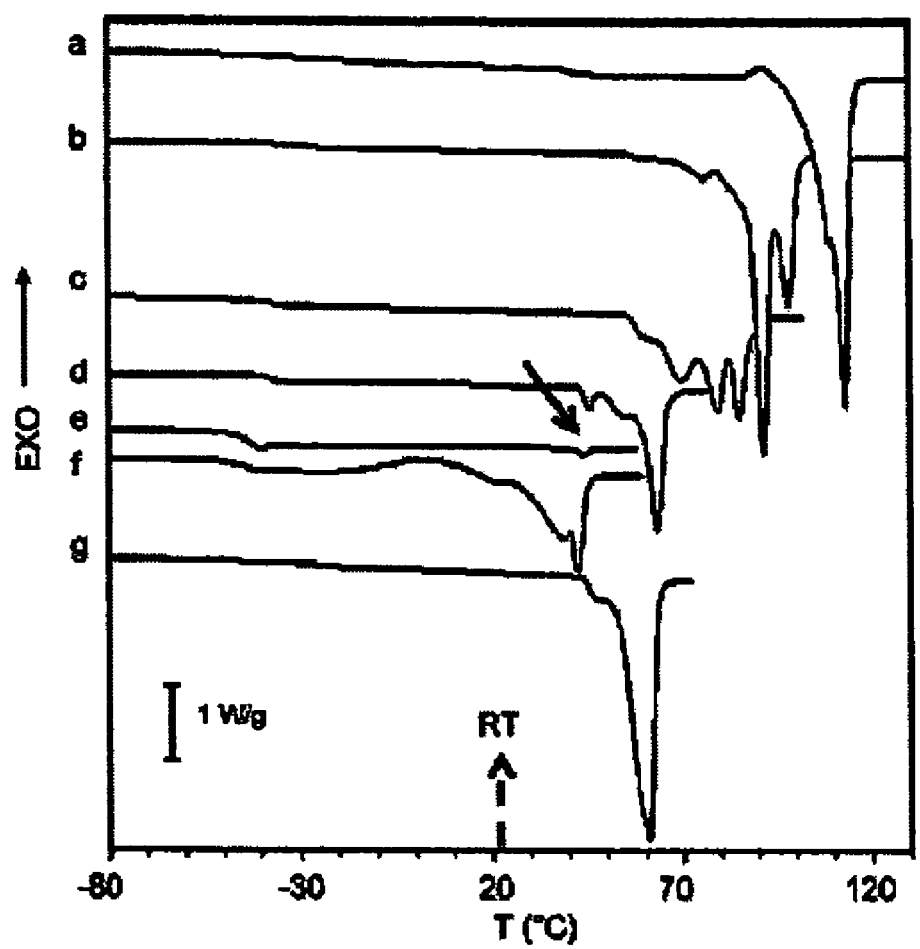
FIG. 10 illustrates first differential scanning calorimetry (DSC) heating scans of PBS (a), poly(BC-co-82 mol % BS) (b), poly(BC-co-69 mol % BS) (c), poly(BC-co-50 mol % BS) (d), poly(BC-co-29 mol % BS) (e), poly(BC-co-14 mol % BS) (f), and PBC (g).

FIG. 10 illustrates the melting behavior of homopolymers and copolymers via DSC heating scans. In particular, curve (e) represents a small melting endotherm lacking a crystal phase, and is a sticky material at RT. In addition, the temperature location of the melting process with respect to room temperature, RT, plays a direct role in the physical structure of these materials. Copolymers with BC units up to 50 mol % melt well above RT and are semicrystalline solids at RT, whereas poly(BC-co-14 mol % BS) is waxy, owing to a fraction of poorly ordered crystals that begin to melt below RT, indicated by curve (f). Also, the small melting endotherm of poly(BC-co-29 mol % BS) is indicated by the solid arrow. The broken arrow marks room temperature (RT). Broken lines are used as guidelines to highlight the endothermal and exothermal phenomena.

FIG. 11 illustrates the crystallization process and to erase effects of thermal history on polymer morphology as the polymers were cooled from the melt at 1° C./min and subsequently reheated at 20° C./min. Selected crystallization and melting curves are shown in parts A and B of FIG. 11, respectively, while Table 6 describes crystallization and melting data of the DSC heating curves after cooling.

TABLE 6

Melting and Crystallization Data from DSC Heating Curves after Cooling at 10° C./min

| sample | $T_c$ (° C.) | $\Delta H_c$ (J/g) | $T_m$ (° C.) | $\Delta H_m$ (J/g) |
|---|---|---|---|---|
| PBC | 33 | 26 | 61 | 34 |
| poly(BC-co-14 mol % BS)[a] | — | — | — | — |
| poly(BC-co-29 mol % BS)[a] | — | — | — | — |
| poly(BC-co-50 mol % BS) | 42 | <1 | 69 | <1 |
| poly(BCco-69 mol % BS) | 57 | 13 | 83 | 53 |
| poly(BC-co-82 mol % BS) | 77 | 7 | 98 | 67 |
| PBS | 95 | 9 | 113 | 79 |

[a]The two copolymers do not crystallize or melt.

Figure 11A:
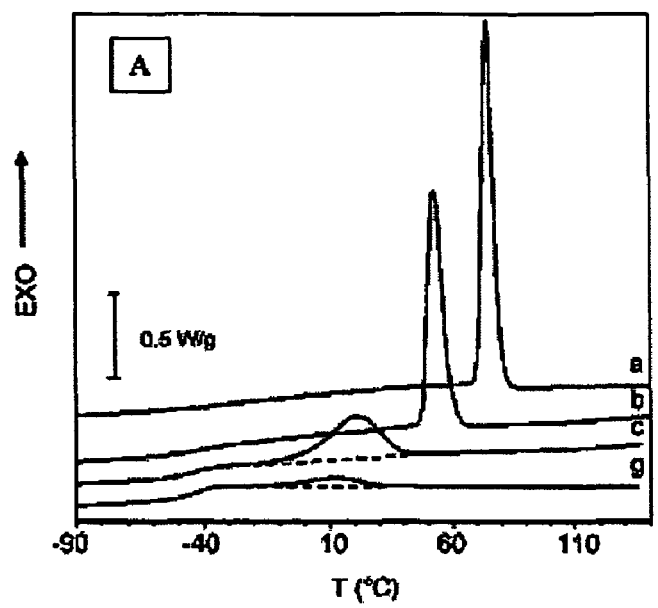
FIG. 11 illustrates DSC scans wherein FIG. 11A describes cooling from melt at 10° C./min and FIG. 11B describes subsequent heating at 20° C./min the following: PBS (a), poly(BC-co-82 mol % BS) (b), poly(BC-co-69 mol % BS) (c), poly(BC-co-50 mol % BS) (d), poly(BC-co-29 mol % BS) (e), poly(BC-co-14 mol % BS) (f), and PBC (g).
Figure 11B:
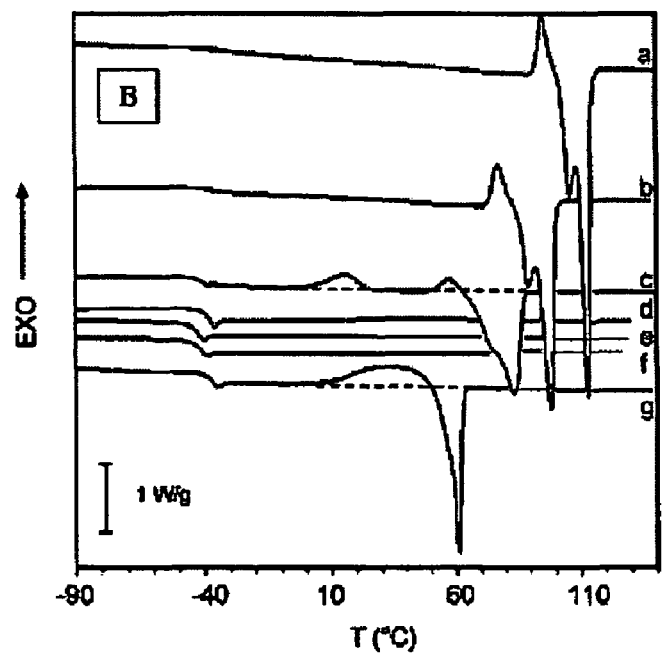

The DSC results of the cooling run (selected curves) are reported in FIG. 11A. The crystallization behavior of the homopolymers are distinct because PBS curve (a) displays a sharp and intense crystallization peak (($\Delta H_c$) 75 J/g) wherein PBC curve (g) displays a broader and much smaller exotherm (($\Delta H_c$) 8 J/g). From the experiments, it was readily shown that only copolymers rich in BS units crystallize. FIG. 11B reported reheating DSC heating scans. Herein, the amorphous copolymers display a well-defined glass transition around −40° C., indicated in curves (d)-(f).

The samples that develop crystallinity during the cooling run, as provided in curves (a)-(c) in FIG. 11A exhibit additional cold crystallization in subsequent heating scans (see exotherms in curves (a)-(c) and (g) in FIG. 11B). As such, FIG. 11 is indicative of crystals formed during both cooling and subsequent heating. Therefore, the values for enthalpy described in Table 6 correspond to the sum of the enthalpies of the two crystallization phenomena.

TABLE 7

Glass Transition Data from DSC Heating Curves after Quench Cooling

| sample | $T_g$ (° C.) | $\Delta C_p$ (J/(g ° C.)) |
|---|---|---|
| PBC | −38 | 0.56 |
| poly(BC-co-14 mol % BS) | −43 | 0.60 |
| poly(BC-co-29 mol % BS) | −44 | 0.65 |
| poly(BC-co-50 mol % BS) | −39 | 0.58 |
| poly(BC-co-69 mol % BS) | −42 | 0.65 |
| poly(BC-co-82 mol % BS) | −34 | 0.28 |
| PBS | −34 | 0.30 |

Table 7 illustrates the glass-to-rubber transition of poly (BC-co-BS) copolymers investigated by DSC on melt quenched samples. Table 7 lists values and corresponding heat capacity increments ($\Delta C_p$). Analysis of $\Delta C_p$ data reveals that, after quench cooling from the melt, most samples show values typical of completely amorphous polymers ($\Delta C_p$ around 0.6 J/(g ° C.)), while high molar BS units, such as PBS and poly(BC-co-82 mol % BS) display lower $\Delta C_p$ values interpreted as a fraction of the polymer being in the crystalline state. These trends are in agreement with previous experimental results discussing the high crystallizing ability of PBS and PBS-rich copolymers as discussed above.

Moreover, Table 7 shows that $T_g$ values of all amorphous samples lie around −40° C. and seem to be uncorrelated with changes in copolymer composition, while the $T_g$ of the partially crystalline samples are slightly higher at −34° C. It is well-established that the glass transition temperature increases in semicrystalline polymers in comparison to fully amorphous polymers. From the results, an assessment is likely that the $T_g$ of fully amorphous PBS might be close to that of amorphous PBC. As such, the similarity of the two homopolymer's $T_g$ indicates the lack of a clear composition dependence of glass transitions for poly(BC-co-BS) copolymers.

Example 3

Aliphatic polycarbonates can be biodegradable materials with potentially important medical applications. They can also be used as thermoplastic additives and as matrix materials in solid electrolytes. High molecular weight aliphatic polycarbonates are suitable for production of extrudates, films, and molded articles. Hydroxyl-terminated aliphatic polycarbonates can be useful and have been widely used in industry as building blocks to produce specialty polyurethanes and other polymeric materials. In addition, polymer membranes prepared from polyimides containing aliphatic polycarbonate segments were reported to be effective for selective separation of aromatic/saturated-hydrocarbon mixtures.

This detailed description of the preferred embodiments and the appended figures have been presented only for illustrative and descriptive purposes, are not intended to be exhaustive and are not intended to limit the scope and spirit of the invention. The embodiments were selected and described to best explain the principles of the invention and its practical applications, and one skilled in the art will recognize that many variations can be made to the invention disclosed herein without departing from the scope and spirit of the invention.

What is claimed is:

1. A method for preparing a poly(carbonate-co-ester) polymer by enzyme catalysis comprising:
    (a) selecting reactants for a reaction such that a first reactant is a dialkyl carbonate, a second reactant is an aliphatic diester, a third reactant is an aliphatic diol or triol reactant, and a fourth reactant is a cyclic lactone, and combining the reactants as a reaction mixture;
    (b) selecting a catalyst capable of catalyzing an ester hydrolysis reaction in an aqueous environment;
    (c) adding the catalyst to the reaction mixture and allowing polymerization to proceed; and
    (d) isolating the product poly(carbonate-co-ester).

2. The method according to claim 1, wherein carbonate units along chains are formed by reactions between diols/triols and alkyl carbonates and ester repeat units are formed by lactone ring-opening.

3. The method according to claim 2, wherein the dialkyl carbonate has the formula $CO(OR)_2$ wherein R represents a straight-chain or branched C1-C5-alkyl ($C_nH_{2n+1}$).

4. The method according to claim 2, wherein the aliphatic ester has the formula $R—((CO)—R1)_2$ wherein R represents a generalized group.

5. The method according to claim 2, wherein the aliphatic diol or triol has the formula HO—R—OH wherein R represents a generalized group.

6. The method according to claim 2, wherein the lactones are selected from the group consisting of ε-caprolactone, para-dioxanone, glycolide, macrolactones, ω-pentadecalactone, and other lactones capable of preparing polyesters by enzyme-catalyzed lactone ring-opening polymerizations.

7. The method according to claim 3, wherein the dialkyl carbonate is selected from the group consisting of: dimethyl, diethyl, di(n-propyl), di(n-butyl), di(sec-butyl), diisobutyl, di(tert-butyl), di(n-pentyl), diisoamyl, and dineopentyl carbonates.

8. The method according to claim 4, wherein the aliphatic ester is selected from the group consisting of: linear or branched hydrocarbon groups having 3-10 carbon atoms; linear or branched C4-C8 diacids; and a mixture of diacids.

9. The method according to claim 5, wherein the aliphatic diol is selected from the group consisting of: 1,2-ethanediol, 1,3-propanediol, 1,4-butanediol, 1,6-hexanediol, 1,5-pentanediol, 1,10-decanediol, 2-methyl-1,3-propanediol, 2-methyl-2-butyl-1,3-propanediol and 2,2-dimethyl-1,4-butanediol, neopentylglycol hydroxypivalate, diethylene glycol, triethylene glycol, and methyldiethanolamine.

10. The method according to claim 5, wherein the triol has 2 primary hydroxyl groups forming a linear polycarbonate polyol.

11. The method according to claim 5, wherein the triol has 3 primary hydroxyl groups forming a hyper-branched polymer.

12. The method according to claim 5, wherein the triol is glycerol or tris-hydroxymethyl ethane.

13. The method according to claim 2, wherein the reaction temperature of the method is $\leq 100°$ C.

14. The method according to claim 2, wherein the first stage is pressurized under low vacuum and the second stage is pressured under high vacuum.

15. The method according to claim 2, wherein the copolymer is poly(BC-co-BS), has a polydisperity between 1.7 and 2.0, upon completion has a molecular weight $\geq 9\,800$, and has a random or block distribution of BC and BS units.

16. The method according to claim 15, wherein the highest molecular weight of the copolymer upon completion of the reaction is derived at a reaction temperature of approximately 80° C.

17. The method according to claim 2, wherein the copolymer is poly(HC-co-HA), has a polydisperity between 1.5 and 1.6, upon completion has a molecular weight $\geq 14\,800$, and has a random or block distribution of HC and HA units.

18. The method according to claim 17, wherein a molecular weight of the copolymer gradually increases as temperature increases.

19. The method according to claim 1, wherein the enzyme is selected from the group consisting of lipases and cutinases.

20. The method according to claim 15, wherein end-group structures of poly(BC-co-BS) are defined by:
    (a) fixing the molar ratio of DES to BD at 0.5:1; and
    (b) varying the molar ratio of DEC to (BD-DES) while (BD-DES) remains constant,
    wherein the content of hydroxyl end groups in polymer chains are decreased and the content of ethyl carbonate plus ethyl ester end groups in copolymers are increased.

* * * * *